(12) United States Patent
Parkash

(10) Patent No.: US 7,816,579 B2
(45) Date of Patent: Oct. 19, 2010

(54) METAL RESISTANT PLANTS, METHODS OF MANUFACTURE, AND METHODS OF USE THEREOF

(75) Inventor: Om Parkash, Amherst, MA (US)

(73) Assignee: The University of Massachusetts, Boston, MA (US)

( * ) Notice: Subject to any disclaimer, the term of this patent is extended or adjusted under 35 U.S.C. 154(b) by 347 days.

(21) Appl. No.: 12/034,248

(22) Filed: Feb. 20, 2008

(65) Prior Publication Data

US 2008/0229444 A1 Sep. 18, 2008

Related U.S. Application Data

(60) Provisional application No. 60/890,730, filed on Feb. 20, 2007.

(51) Int. Cl.
*A01H 5/00* (2006.01)
*A01H 5/10* (2006.01)
*C12N 15/09* (2006.01)
*C12N 15/29* (2006.01)
*C12N 15/82* (2006.01)

(52) U.S. Cl. .................. 800/278; 800/317; 800/320; 800/298; 800/306; 435/468; 435/430.1

(58) Field of Classification Search ............... None
See application file for complete search history.

(56) References Cited

U.S. PATENT DOCUMENTS

2005/0198707 A1 9/2005 Meagher et al.
2005/0216976 A1 9/2005 Meagher et al.

FOREIGN PATENT DOCUMENTS

| WO | 8700551 | 1/1987 |
|---|---|---|
| WO | 0248335 A2 | 6/2002 |
| WO | 2005070088 A2 | 8/2005 |

OTHER PUBLICATIONS

Salt et al. Biotechnology, vol. 13, pp. 468-474, 1995.*
Guerinot et al. Plant Physiology (2001), vol. 125, pp. 164-167.*
Goldsbrough (2000). Metal Tolerance in Plants: The Role of Ohtrochelins and Metallothions, CRC Press, Boca, FL. 221-233.*
U.S. Appl. No. 12/125,362 to Parkash; filed May 22, 2008; Title: Metal Resistant Plants, and Methods of Manufacture Thereof; copy may be found in PAIR.
Altschul et al; "Gapped BLAST and PSI-BLAST: a New Generation of Protein Database Search Programs"; Nucleic Acids Research; 25; pp. 3389-3402; (1997).
Baluska; "Plant Formins Come of Age: Something Special About Cross-Walls"; New Phytologist; 168; pp. 499-503; (2005).
Dhankher; "Arsenic Metabolism in Plants: An Inside Story"; New Phytologist; 168; pp. 503-505; (2005).
Dhankher, et al; "Engineering Tolerance and Hyperaccumulation of Arsenic in Plants by Combining Arsenate Reductase and Y-Glutamylcysteine Synthetase Expression"; Nature Biotechnology; 20; pp. 1140-1145; (2002).
Dhankher, et al; Hyperaccumulation of Arsenic in the Shoots of Arabidopsis Silenced for Arsenate Reductase (ACR2); PNAS; 103; pp. 5413-5418; (2006).
Karlin, et al; "Methods for Assessing the Statistical Significance of Molecular Sequence Features by Using General Scoring Schemes"; PNAS; 87; pp. 2264-2268; (1990).
Li et al; "Arsenic and Mercury Tolerance and Cadmium Sensitivity in Arabidopsis Plants Expressing Bacterial γ-Glutamylcysteine Synthetase"; Environmental Toxicology and Chemistry; 24; pp. 1376-1386; (2005).
Pannell; "Phenotypic Plasticity and a Functional VS Genetic Perspective of Plant Gender"; New Phytologist; 168; pp. 506-510; (2005).
Williams et al; "Variation in Arsenic Speciation and Concentration in Paddy Rice Related to Dietary Exposure"; Environ. Sci. Technol.; 39; pp. 5531-5540; (2005).
Database EMBL (online), Dec. 13, 2002, "Arabidopsis thaliana At5g03455 mRNA for unknown protein, complete cds, clone: RAFL19-08-B21.", XP002484347; retrieved from EBI accession No. EMBL:AK117898, Database accession No. AK117898, Abstract, 2 pages.
International Search Report and Written Opinion; International Application No. PCT/US2008/002181; International Filing Date Feb. 20, 2008; Applicant's File Reference UMA-0003-F-PCT, Date of Mailing Jun. 25, 2008; 14 pages.
Altschul, et al.; "Basic Local Alignment Search Tool"; J. Mol. Biol.; 215; pp. 403-410; (1990).
Jin, et al.; "Phylogenetic and Expression Analysis of ZnF-AN1 Genes in Plants"; Genomics; 90; pp. 265-275; (2007).
Saurin, et al.; Does This Have a Familiar RING?; Trends Biochem. Sci.; 21; pp. 208-214; (1996).
Sok, et al.; "Rsenite-Inducible RN -Associated Protein ( IR P) Protects Cells From Arsenite Toxicity"; Cell Stress & Chaperones; 6; pp. 6-15; (2001).
Vij, et al.; "Genome-wide Analysis of the Stress Associated Protein (SAP) Gene Family Containing A20/AN1 Zinc-Finger(s) in Rice and Their Phylogenetic Relationship With Arabidopsis"; Mol. Gen. Genomics; 276; pp. 565-575; (2006).

* cited by examiner

Primary Examiner—Medina A Ibrahim
(74) Attorney, Agent, or Firm—Cantor Colburn LLP

(57) ABSTRACT

Disclosed herein is a transgenic plant transformed with an isolated polynucleotide comprising a plant arsenate reductase coding sequence operatively linked to a plant-expressible transcription regulatory sequence. Also disclosed are methods to limit metal or metal ion accumulation in a harvested plant tissue comprising growing the transgenic plant; and harvesting plant tissue having reduced metal or metal ion accumulation. Further disclosed herein is method of making a transgenic plant transformed with an isolated polynucleotide comprising a plant arsenate reductase coding sequence operatively linked to a plant-expressible transcription regulatory sequence.

44 Claims, 9 Drawing Sheets

150 μM Arsenate

WC3110 (-ArsC)          WC3110 (-ArsC)
+ pBS                   + OsACR2;1

PROLIFERATING CALLUS          REGENERATED RICE PLANTLETS

METAL RESISTANT PLANTS, METHODS OF MANUFACTURE, AND METHODS OF USE THEREOF

CROSS REFERENCE TO RELATED APPLICATION

This application claims the benefits of U.S. Provisional Patent Application Ser. No. 60/890,730 filed Feb. 20, 2007, which is fully incorporated herein by reference.

BACKGROUND

Arsenic (As) is an extremely toxic carcinogenic metalloid pollutant that adversely affects the health of millions of people worldwide. Inorganic forms of arsenic, such as arsenate ($AsO_4^{3-}$) and arsenite ($AsO_3^{3-}$), are more toxic than organic forms of arsenic and cause cancer. Arsenic poisoning can occur via ingestion of contaminated drinking water and food. Industrial pollution and agricultural practices including the use of arsenic in pesticides, herbicides, fertilizers, wood preservatives, mining, and irrigation with contaminated groundwater have significantly arsenic levels in agricultural soil. The arsenic contaminated soil, sediment, and water supplies are major sources of contamination in the food chain. There is global concern regarding arsenic contamination in drinking water and soil, particularly on the Indian subcontinent where more than 450 million people are at risk for arsenic poisoning.

There are many different ways arsenic can enter the food chain. Plants grown on arsenic contaminated soil can accumulate high levels of arsenic in roots, shoots, and grain. Arsenic uptake by plants may play an important role in the introduction of arsenic into the food chain, for example, by the direct ingestion of arsenic contaminated grain. In addition, arsenic contaminated straw that is used as cattle feed may have adverse health effects on cattle and may result in an increased arsenic exposure in humans via a plant-animal-human pathway. There is, therefore, concern regarding the accumulation of arsenic in meat and dairy products as well as in agricultural crops and vegetables.

In addition, arsenic is phytotoxic and causes significant loss in crop yields. Arsenate is a phosphate analog and competes with phosphate for uptake in plants causing the inhibition of phosphate and other nutrients. Thus, arsenic contamination is an agricultural concern.

Arsenic is present in the environment in different forms. The arsenate oxyanions, $HAsO_4^{2-}$ and $H_2AsO_4^-$, are the most prevalent forms of arsenic in surface soil, water, and within cells, and these oxyanions contain arsenic in the pentavalent state [As(V)]. Arsenite, which at neutral pH contains arsenic in the trivalent oxidation state [As(III)] and likely as the acid $HAsO_3^{2-}$, is highly reactive and readily forms As(III)-thiol complexes. Plants use arsenate reductases to detoxify arsenic by reducing As(V) to As(III), which is subsequently detoxified via forming complexes with thiol-reactive peptides such as γ-glutamylcysteine (γ-EC), glutathione (GSH) and phytochelatins (PCs). It is suggested that these AsIII-thiol complexes are then sequestered into vacuoles by glutathione-conjugating pumps. It is further believed that plants trap arsenite in below ground tissues in order to prevent access to aboveground reproductive tissues to prevent possible mutagenic consequences.

The structure and function of arsenate reductases, particularly bacterial arsenate reductases, has been studies extensively. Arsenate reductases reduce arsenate [As(V)] to arsenite [As(III)]. Arsenate reductases include a P-loop with a characteristic $CX_5R$ sequence motif flanked by a beta-strand and an alpha-helix. The arsenate substrate undergoes a nucleophilic attack by the thiol of the cysteine in the P-loop. A hydroxyl then leaves the arsenic, leading to a covalent Cys-HAsO intermediate. The nucleophilic displacement is followed by an intramolecular disulfide bond cascade with two other redox-active cysteines in which arsenite is released and an intramolecular disulfide bond is formed. After completion of the reaction, the arsenate reductase is regenerated by thioredoxin that reduces the disulfide bond formed during the reaction. Arsenate reductases are very efficient at detoxifying arsenate ions.

There is a strong need to reduce the arsenic uptake in food crops and the subsequent introduction of arsenic into the food chain. There further is a need to develop crops that are resistant to arsenic.

SUMMARY

Disclosed herein is a transgenic plant transformed with a recombinant polynucleotide, the recombinant polynucleotide comprising an isolated plant arsenate reductase coding sequence operatively linked to a plant-expressible transcription regulatory sequence.

Disclosed herein also is a method of limiting metal or metal ion accumulation in a harvested plant tissue comprising growing a transgenic plant expressing a recombinant polynucleotide, the recombinant polynucleotide comprising an isolated plant arsenate reductase coding sequence operatively linked to a plant-expressible transcription regulatory sequence; and harvesting a plant tissue from the transgenic plant.

Further disclose is a method for producing a metal ion resistant plant comprising introducing a recombinant polynucleotide comprising an plant arsenate reductase coding sequence operatively linked to a plant-expressible transcription regulatory sequence into a plant cell or a plant tissue; producing a transgenic plant cell or tissue comprising the recombinant polynucleotide; and regenerating the transgenic plant cell or transgenic plant tissue to provide a metal ion resistant plant.

DETAILED DESCRIPTION

Figure 1:
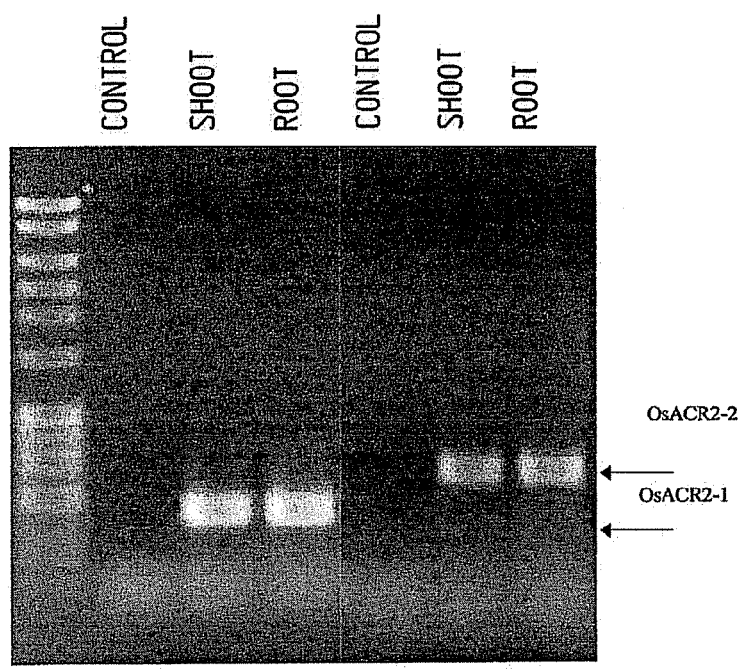
FIG. 1 shows the expression of OsACR cDNAs in rice.

Disclosed herein are plant arsenate reductases and methods of use thereof. In one embodiment, provided is a transgenic plant transformed with a recombinant polynucleotide, the recombinant polynucleotide comprising a plant arsenate reductase coding sequence operatively linked to a plant-expressible transcription regulatory sequence. The inventors have discovered that the increased expression of a plant arsenate reductase gene in a transgenic plant dramatically increases the arsenic resistance of the transgenic plants. These transgenic plants also accumulate much less total arsenic in their above ground tissue as compared to wild type plants. The transgenic plants thus have reduced arsenic uptake and translocation into the above ground tissue. The reduction in total arsenic accumulation in above ground tissue allows the harvesting of plant tissue having reduced amounts of arsenic. Accordingly, the use of harvested transgenic plant tissue in food for humans or livestock will reduce the amount of arsenic introduced into the food chain. For example, transgenic rice plants will have less arsenic in seed grains and in shoots, thereby providing safer rice grains for human consumption, and safer rice straw for livestock feed. Further, arsenic being phytotoxic to plants, severely affect crop yields. The transgenic plants are resistant to arsenic and provide for improved crop yields in arsenic contaminated soil. For example, the transgenic rice plants have 6-7 fold higher levels of arsenic resistance, thus rice yield will be significantly higher as compared to control non-transgenic rice. An additional advantage is that the reduction in arsenic uptake also results in increased phosphate uptake by the plants, thereby further improving plant productivity and requiring fewer applications of phosphate-containing fertilizer.

In one embodiment, the transgenic plants further comprise a recombinant polynucleotide suitable for expression of a coding sequence for an enzyme involved in the biosynthesis of the phytochelatins. Phytochelatins are peptides of higher plants having a general structure of $(\gamma\text{-Glu-Cys})_n\text{-Gly}$, where n equals 2 to 11. Phytochelatins are synthesized in plants in response to the presence of heavy metals and form stable complexes with metal ions. Exemplary phytochelatin biosynthetic enzymes include γ-ECS (γ-glutamylcysteine synthase), GS (glutathione synthase), and PCS (phytochelatin synthase). In one embodiment, both arsenate reductase and phytochelatin biosynthetic enzyme recombinant genes (transgenes) are combined in a single plant genome by cotransformation of two constructs, by sequential transformation, or by cross-breeding singly transformed plants, each containing one of the genetic constructs of interest, with selection for progeny having both the arsenate reductase coding sequence and the phytochelatin biosynthetic coding sequence. In another embodiment, two or more transgenes are combined in a single plant by conventional breeding and screening (phenotypic or for molecular markers) to obtain the plant that express both the recombinant arsenate reductase gene and the recombinant phytochelatin biosynthetic enzyme gene.

The inventors have unexpectedly discovered that plants, such as *Arabidopsis thaliana* and rice (*Oryza sativa*), genetically engineered to express a plant arsenate reductase gene, demonstrate improved arsenic resistance. Similar results are obtainable in other plants, including monocots, dicots and gymnosperms, after stable transformation and regeneration. Suitable plants also include field crops, fruits, and vegetables such as canola, sunflower, tobacco, mustard, crambe, sugar beet, cotton, maize, wheat, barley, rice, sorghum, mangelwurzels, tomato, mango, peach, apple, pear, strawberry, banana, melon, potato, carrot, lettuce, cabbage, onion, soybean, sugar cane, pea, field beans, poplar, grape, citrus, alfalfa, rye, oats, turf and forage grasses, flax and oilseed rape, nut producing plants, bioenergy plants such as *Brachypodium distachyon* and switchgrass (*Panicum virgatum*), and the like. Exemplary plants include *Arabidopsis thaliana*, rice (*Oryza sativa*), *Brassica* spp., and *Crambe abyssinica*.

As used herein, the term "arsenic resistance" means that a non-naturally occurring organism (e.g., a transgenic plant) is not inhibited by the presence of at least one ionic form of arsenic at concentrations (levels) at that a naturally occurring (wild-type) counterpart of the non-naturally occurring organism is inhibited or exhibits symptoms of toxicity. It is not intended that the term arsenic resistance refer to resistance to unlimited concentrations of arsenic ions, but rather the term is relative in that it relies on comparison to the properties of a parental strain. Resistance to other metal ions is analogous and is referred to as "metal resistance." In one embodiment, an arsenic resistant organism is resistant to a concentration of greater than or equal to about 50 micromolar arsenic in an ionic form. Specifically, an arsenic resistant organism is resistant to a concentration of greater than or equal to about 100 micromolar arsenic in an ionic form. More specifically, an arsenic resistant organism is resistant to a concentration of greater than or equal to about 500 micromolar arsenic in an ionic form. Even more specifically, an arsenic resistant organism is resistant to a concentration of greater than or equal to about 1 millimolar arsenic in an ionic form.

An "arsenic resistance coding sequence" is one that encodes a protein capable of mediating resistance to at least one arsenic ion, including, but not limited to, oxyanions of arsenic. Suitable arsenic resistance coding sequences include coding sequences for arsenate reductases. Also within the scope of this definition are mutant sequences that encode proteins capable of mediating resistance to oxyanions of arsenic or other arsenic-containing ions or ion complexes. Suitable arsenic resistance coding sequences include the *Arabidopsis thaliana* ACR2 sequence, the rice ACR2-1 sequence, the rice ACR2-2 sequence, the *Brassica napus* (rape) ACR2, and the *Crambe abyssinica* (a close relative of *Brassica*) ACR2 sequences.

In one embodiment, included herein are isolated arsenate reductase polynucleotides. An isolated polynucleotide is a polynucleotide the structure of which is not identical to that of any naturally occurring polynucleotide or to that of any fragment of a naturally occurring genomic polynucleotide spanning more than three separate genes. The term therefore covers, for example, (a) a DNA that has the sequence of part of a naturally occurring genomic DNA molecule but is not flanked by both of the coding or noncoding sequences that flank that part of the molecule in the genome of the organism in that it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

In one embodiment, the arsenate reductase comprises the *Arabidopsis thaliana* AtACR2 sequence (nucleotide sequence SEQ ID NO:1, Accession number NM_120425.2; polypeptide sequence SEQ ID NO:5, Accession number NP_568119.1). In another embodiment, the arsenate reductase comprises the rice OsACR2-1 sequence (nucleotide sequence SEQ ID NO:2, NM_197615.1; polypeptide sequence SEQ ID NO:6, Accession number NP_922597.1). In another embodiment, the arsenate reductase comprises the rice OsACR2-2 sequence (nucleotide sequence SEQ ID NO:3, Accession number NM_187653.1; polypeptide sequence SEQ ID NO:7, Accession number NP_912542.1). In another embodiment, the arsenate reductase comprises the *Brassica napus* ACR2 (BnACR2) sequence (nucleotide sequence SEQ ID NO:4, Accession number CD821288; polypeptide sequence SEQ ID NO:8.) In another embodiment, the arsenate reductase comprises the *Crambe abyssinica* ACR2 (CaACR2) sequence (nucleotide sequence SEQ ID NO:21; polypeptide sequence SEQ ID NO:22.) An arsenate reductase includes an arsenate reductase homologous to AtACR2, OsACR2-1, OsACR2-2, BnACR2, or CaACR2 so long as the arsenate reductase has arsenate reductase activity. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog" meaning a polynucleotide or polypeptide that is the functional equivalent of a polynucleotide or polypeptide in another species, and "paralog" meaning a functionally similar sequence when considered within the same species. Paralogs present in the same species or orthologs of the AtACR2 gene in other plant species can readily be identified without undue experimentation, by molecular biological techniques well known in the art. As used herein, AtACR2, OsACR2-1, OsACR2-2, BnACR2, and CaACR2 refers to AtACR2, OsACR2-1, OsACR2-2, BnACR2, and CaACR2, respectively, as well as their homologs and orthologs.

As used herein, "percent homology" of two amino acid sequences or of two nucleic acid sequences is determined using the algorithm of Karlin and Altschul (1990) *Proc. Natl. Acad. Sci., U.S.A.* 87: 2264-2268. Such an algorithm is incorporated into the NBLAST and XBLAST programs of Altschul et al. (1990) *J. Mol. Biol.* 215: 403-410. BLAST nucleotide searches are performed with the NBLAST program, score=100, word length 12, to obtain nucleotide sequences homologous to a nucleic acid molecule of the invention. BLAST protein searches are performed with the XBLAST program, score=50, word length=3, to obtain amino acid sequences homologous to a reference polypeptide (e.g., SEQ ID NO:5). To obtain gapped alignments for comparison purposes, Gapped BLAST is utilized as described in Altschul et al. (1997) *Nucleic Acids Res.* 25: 3389-3402. When utilizing BLAST and Gapped BLAST programs, the default parameters are typically used. (See www.ncbi.nlm.nih.gov)

In addition, polynucleotides that are substantially identical to a polynucleotide encoding an AtACR2, OsACR2-1, OsACR2-2, BnACR2, or CaACR2 polypeptide are included. By "substantially identical" is meant a polypeptide or polynucleotide having a sequence that is at least about 85%, specifically about 90%, and more specifically about 95% or more identical to the sequence of the reference amino acid or nucleic acid sequence. For polypeptides, the length of the reference polypeptide sequence will generally be at least about 16 amino acids, or specifically at least about 20 amino acids, more specifically at least about 25 amino acids, and most specifically at least about 35 amino acids. For nucleic acids, the length of the reference nucleic acid sequence will generally be at least about 50 nucleotides, specifically at least about 60 nucleotides, more specifically at least about 75 nucleotides, and most specifically at least about 110 nucleotides.

Typically, homologous sequences can be confirmed by hybridization, wherein hybridization under stringent conditions. Using the stringent hybridization (i.e., washing the nucleic acid fragments twice where each wash is at room temperature for 30 minutes with 2× sodium chloride and sodium citrate (SCC buffer; 1.150. mM sodium chloride and 15 mM sodium citrate, pH 7.0) and 0.1% sodium dodecyl sulfate (SDS); followed by washing one time at 50° C. for 30 minutes with 2×SSC and 0.1% SDS; and then washing two times where each wash is at room temperature for 10 minutes with 2×SCC), homologous sequences can be identified comprising at most about 25 to about 30% base pair mismatches, or about 15 to about 25% base pair mismatches, or about 5 to about 15% base pair mismatches.

Polynucleotides encoding AtACR2, OsACR2-1, OsACR2-2, BnACR2, or CaACR2 sequences allow for the preparation of relatively short DNA (or RNA) sequences having the ability to specifically hybridize to such gene sequences. The short nucleic acid sequences may be used as probes for detecting the presence of complementary sequences in a given sample, or may be used as primers to detect, amplify or mutate a defined segment of the DNA sequences encoding a AtACR2, OsACR2-1, OsACR2-2, BnACR2, or CaACR2 polypeptide. A nucleic acid sequence employed for hybridization studies may be greater than or equal to about 14 nucleotides in length to ensure that the fragment is of sufficient length to form a stable and selective duplex molecule. Such fragments are prepared, for example, by directly synthesizing the fragment by chemical means, by application of nucleic acid reproduction technology, such as PCR technology, or by excising selected nucleic acid fragments from recombinant plasmids containing appropriate inserts and suitable restriction sites.

The term plant arsenate reductase includes polynucleotides that encode the AtACR2, OsACR2-1, OsACR2-2, BnACR2, and CaACR2 polypeptides or full-length proteins that contain substitutions, insertions, or deletions into the polypeptide backbone. Related polypeptides are aligned with AtACR2, OsACR2-1, OsACR2-2, BnACR2, and CaACR2 by assigning degrees of homology to various deletions, substitutions and other modifications. Homology can be determined along the entire polypeptide or polynucleotide, or along subsets of contiguous residues. The percent identity is the percentage of amino acids or nucleotides that are identical when the two sequences are compared. The percent similarity is the percentage of amino acids or nucleotides that are chemically similar when the two sequences are compared. AtACR2, OsACR2-1, OsACR2-2, BnACR2, or CaACR2, and homologous polypeptides are preferably greater than or equal to about 75%, preferably greater than or equal to about 80%, more preferably greater than or equal to about 90% or most preferably greater than or equal to about 95% identical.

A homologous polypeptide may be produced, for example, by conventional site-directed mutagenesis of polynucleotides (which is one avenue for routinely identifying residues of the molecule that are functionally important or not), by random mutation, by chemical synthesis, or by chemical or enzymatic cleavage of the polypeptides.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

Reference herein to either the nucleotide or amino acid sequence of AtACR2, OsACR2-1, OsACR2-2, BnACR2, and CaACR2 also includes reference to naturally occurring variants of these sequences. Non-naturally occurring variants that differ from SEQ ID NOs:1-4 (nucleotide) and 5-8 (amino acid) and retain biological function are also included herein. Preferably the variants comprise those polypeptides having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. Whether an amino acid change results in a functional polypeptide can readily be determined by assaying the properties of transgenic plants containing the AtACR2, OsACR2-1, OsACR2-2, BnACR2, and CaACR2 derivatives.

Reference to AtACR2, OsACR2-1, OsACR2-2, BnACR2, and CaACR2 also refers to polypeptide derivatives of AtACR2, OsACR2-1, OsACR2-2, BnACR2, and CaACR2. As used herein, "polypeptide derivatives" include those polypeptides differing in length from a naturally-occurring AtACR2, OsACR2-1, OsACR2-2, BnACR2, and CaACR2 and comprising about five or more amino acids in the same primary order as is found in AtACR2, OsACR2-1, OsACR2-2, BnACR2, and CaACR2. Polypeptides having substantially the same amino acid sequence as AtACR2, OsACR2-1, OsACR2-2, BnACR2, and CaACR2 but possessing minor amino acid substitutions that do not substantially affect the ability of AtACR2, OsACR2-1, OsACR2-2, BnACR2, and CaACR2 polypeptide derivatives to interact with AtACR2, OsACR2-1, OsACR2-2, BnACR2, and CaACR2-specific molecules, respectively, such as antibodies, are within the definition of AtACR2, OsACR2-1, OsACR2-2, BnACR2, and CaACR2 polypeptide derivatives. Polypeptide derivatives also include glycosylated forms, aggregative conjugates with other molecules and covalent conjugates with unrelated chemical moieties.

In one embodiment, the arsenate reductase (e.g.,AtACR2, OsACR2-1, OsACR2-2, BnACR2, and CaACR2 genes or their homologs) are expressed in vectors suitable for in vivo expression such as, for example, plant expression systems. The arsenate reductase polynucleotides are inserted into a recombinant expression vector or vectors. The term "recombinant expression vector" refers to a plasmid, virus, or other means known in the art that has been manipulated by insertion or incorporation of the arsenate reductase genetic sequence. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors are transformed into a suitable host cell to form a host cell vector system for the production of a polypeptide.

The term recombinant polynucleotide or nucleic acid refers to a polynucleotide that is made by the combination of two otherwise separated segments of sequence accomplished by the artificial manipulation of isolated segments of polynucleotides by genetic engineering techniques or by chemical synthesis. In so doing, one may join together polynucleotide segments of desired functions to generate a desired combination of functions.

The term transgene refers to a recombinant polynucleotide or nucleic acid that comprises a coding sequence encoding a protein or RNA molecule.

The arsenate reductase polynucleotides are inserted into a vector adapted for expression in a plant, bacterial, yeast, insect, amphibian, or mammalian cell that further comprises the regulatory elements necessary for expression of the nucleic acid molecule in the plant, bacterial, yeast, insect, amphibian, or mammalian cell operatively linked to the nucleic acid molecule encoding arsenate reductase. Suitable vectors for plant expression include T-DNA vectors. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included. If a promoter is inducible, there are sequences present that mediate regulation of expression so that the associated sequence is transcribed only when an inducer (e.g., light) is available to the plant or plant tissue. An exemplary promoter is the *Arabidopsis* ACT2 promoter that is constitutively active and provides high levels of expression of an associated coding sequence.

Other suitable expression control sequences include 3' untranslated sequences located downstream of an associated coding sequence. An exemplary 3' untranslated sequence is that from the ACT2 gene of *Arabidopsis*.

With respect to a coding sequence, the term "plant-expressible" means that the coding sequence (nucleotide sequence) can be efficiently expressed by plant cells, tissue and/or whole plants. As used herein, a plant-expressible coding sequence has a GC composition consistent with acceptable gene expression in plant cells, a sufficiently low CpG content so that expression of that coding sequence is not restricted by plant cells, and codon usage that is consistent with that of plant genes. Where it is desired that the properties of the plant-expressible metal resistance gene are identical to those of the naturally occurring arsenic resistance gene, the plant-expressible homolog will have a synonymous coding sequence or a substantially synonymous coding sequence. A substantially synonymous coding sequence is one in that there are codons that encode similar amino acids to a comparison sequence, or if the amino acid substituted is not similar in properties to the one it replaces, that change has no significant effect on enzymatic activity for at least one substrate of that enzyme. As discussed herein, it is well understood that in most cases, there is some flexibility in amino acid sequence such that function is not significantly changed. Conservative changes in amino acid sequence, and the resultant similar protein can be readily tested using procedures such as those disclosed herein. Where it is desired that the plant-expressible gene have different properties, there can be variation in the amino acid sequence as compared to the wild-type gene, and the properties of arsenic resistance can be readily determined as described herein.

"Plant-expressible transcriptional and translational regulatory sequences" are those that can function in plants, plant tissue and/or plant cells to effect the transcriptional and translational expression of the nucleotide sequences with that they are associated. Included are 5' sequences that qualitatively control gene expression (turn on or off gene expression in response to environmental signals such as light, or in a tissue-specific manner) and quantitative regulatory sequences that advantageously increase the level of downstream gene expression. An example of a sequence motif that serves as a translational control sequence is that of the ribosome binding site sequence. Polyadenylation signals are examples of transcription regulatory sequences positioned downstream of a target sequence. Exemplary flanking sequences include the 3' flanking sequences of the nos gene of the *Agrobacterium tumefaciens* Ti plasmid. The upstream nontranslated sequence of a bacterial merA coding sequence can be utilized to improve expression of other sequences in plants as well.

The plant-expressible transcription regulatory sequence optionally comprises a constitutive promoter to drive gene expression throughout the whole plant or a majority of plant tissues. In one embodiment, the constitutive promoter drives gene expression at a higher level than the endogenous plant gene promoter. In one embodiment, the constitutive promoter drives gene expression at a level that is at least two-fold higher, specifically at least five-fold higher, and more specifically at least ten-fold higher than the endogenous plant gene promoter. Suitable constitutive promoters include plant virus promoters such as the cauliflower mosaic virus (CaMV) 35S and 19S promoters. An exemplary plant virus promoter is the cauliflower mosaic virus 35S promoter. Suitable constitutive promoters further include promoters for plant genes that are constitutively expressed such as the plant ubiquitin, Rubisco, and actin promoters such as the ACT1 and ACT2 plant actin genes. Exemplary plant gene promoters include the ACT2 promoter from *Arabidopsis* (locus AT3G18780; SEQ ID. NO: 12) and the ACT1 promoter from rice (GenBank Accession no. S44221.1; SEQ ID. NO:13).

Where a regulatory element is to be coupled to a constitutive promoter, generally a truncated (or minimal) promoter is used, for example, the truncated 35S promoter of Cauliflower Mosaic Virus. Truncated versions of other constitutive promoters can also be used to provide CAAT and TATA-homologous regions; such promoter sequences can be derived from those of *Agrobacterium tumefaciens* T-DNA genes such as nos, ocs and mas and plant virus genes such as the CaMV 19S gene or the ACT2 gene of *Arabidopsis*. Translational control sequences specifically exemplified herein are the nucleotides between 8 and 13 upstream of the ATG translation start codon for bacterial signals and from nucleotides 1 to 7 upstream of the ATG translation start codon for plants.

A minimal promoter contains the DNA sequence signals necessary for RNA polymerase binding and initiation of transcription. For RNA polymerase II promoters the promoter is identified by a TATA-homologous sequences motif about 20 to 50 base pairs upstream of the transcription start site and a CAAT-homologous sequence motif about 50 to 120 base pairs upstream of the transcription start site. By convention, the nucleotides upstream of the transcription start with increasingly large numbers extending upstream of (in the 5' direction) from the start site. In one embodiment, transcription directed by a minimal promoter is low and does not respond either positively or negatively to environmental or developmental signals in plant tissue. An exemplary minimal promoter suitable for use in plants is the truncated CaMV 35S promoter, that contains the regions from −90 to +8 of the 35S gene. Where high levels of gene expression are desired, transcription regulatory sequences that upregulate the levels of gene expression may be operatively linked to a minimal promoter is used thereto. Such quantitative regulatory sequences are exemplified by transcription enhancing regulatory sequences such as enhancers.

In one embodiment, the plant-expressible transcription regulatory sequence comprises a tissue or organ-specific promoter to drive gene expression in selected organs such as roots or shoots and tissues therein. In one embodiment, the organ-specific promoter drives gene expression in below ground tissues such as roots and root hairs. In one embodiment, the organ-specific promoter drives gene expression in above ground tissues such as shoots and leaves. An exemplary leaf-specific promoter is the SRS1 promoter (SEQ ID. NO:14). In one embodiment, the organ-specific promoter drives gene expression in floral and reproductive tissues.

The plant-expressible transcription regulatory sequence optionally comprises an inducible promoter to drive gene expression in response to selected stimuli. Suitable inducible promoters include a light inducible promoter such as the SRS1 promoter, arsenic inducible promoters such as the OsACR2 promoter, and the chlorophyll A/13 binding protein light-inducible transcription regulatory sequences.

The choice of vector used for constructing the recombinant DNA molecule depends on the functional properties desired, e.g., replication, protein expression, and the host cell to be transformed. In one embodiment, the vector comprises a prokaryotic replicon, i.e., a DNA sequence having the ability to direct autonomous replication and maintenance of the recombinant DNA molecule extra-chromosomally when introduced into a prokaryotic host cell, such as a bacterial host cell. In addition, the vector may also comprise a gene whose expression confers a selective advantage, such as a drug resistance, to the bacterial host cell when introduced into those transformed cells. Suitable bacterial drug resistance genes are those that confer resistance to ampicillin or tetracycline, among other selective agents. The neomycin phosphotransferase gene has the advantage that it is expressed in eukaryotic as well as prokaryotic cells.

Vectors typically include convenient restriction sites for insertion of a recombinant DNA molecule. Suitable vector plasmids include pUC8, pUC9, pBR322, and pBR329 available from BioRad Laboratories (Richmond, Calif.) and pPL, pK and K223 available from Pharmacia (Piscataway, N.J.), and pBLUESCRIPT® and pBS available from Stratagene (La Jolla, Calif.). Suitable vectors include, for example, Lambda phage vectors including the Lambda ZAP vectors available from Stratagene (La Jolla, Calif.). Other exemplary vectors include pCMU. Other appropriate vectors may also be synthesized, according to known methods; for example, vectors pCMU/K$^b$ and pCMUII which are modifications of pCMUIV.

Suitable expression vectors capable of expressing a recombinant nucleic acid sequence in plant cells and capable of directing stable integration within the host plant cell include vectors derived from the tumor-inducing (Ti) plasmid of *Agrobacterium tumefaciens*, and several other expression vector systems known to function in plants. See for example, Verma et al., No. WO87/00551, incorporated herein by reference.

Expression and cloning vectors optionally contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Suitable selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend, in part, on the host cell. In one embodiment, the arsenic resistance coding sequence itself is used as a selectable marker to select transformants on medium supplemented with an appropriate concentration of arsenic.

In one embodiment, the plant arsenate reductase coding sequence is cloned into a vector suitable for expression in *Arabidopsis* and rice under the control of different constitutive promoters including the CaMV 35S promoter and the actin promoters from *Arabidopsis* and rice. In one embodiment, the plant arsenate reductase coding sequence is regulated by an organ or tissue-specific or an inducible promoter. An exemplary tissue-specific promoter is the leaf-specific SRS1 promoter (SEQ ID. NO:14). In one embodiment, the plant arsenate reductase coding sequence is cloned into a plant expression cassette construct or vector comprising a promoter, convenient cloning sites and the nos transcription terminator (NOSt).

Transformation of a host cell with an expression vector or other DNA is carried out by conventional techniques as are well known to those skilled in the art. By "transformation" is meant a permanent or transient genetic change induced in a cell following incorporation of new DNA (i.e., DNA exogenous to the cell). Where the cell is a plant cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding an arsenate reductase (e.g., a AtACR2, OsACR2-1, OsACR2-2, BnACR2, or CaACR2 polypeptide), or fragment thereof.

Recombinant host cells, in the present context, are those that have been genetically modified to contain an isolated DNA molecule. The DNA can be introduced by a means that is appropriate for the particular type of cell, including without limitation, transfection, transformation, lipofection, or electroporation.

Also included herein are transgenic plants that have been transformed with an arsenate reductase gene. A "transgenic plant" is one that has been genetically modified to contain and express recombinant DNA sequences, either as regulatory RNA molecules or as proteins. As specifically exemplified herein, a transgenic plant is genetically modified to contain and express a recombinant DNA sequence operatively linked to and under the regulatory control of transcriptional control sequences that function in plant cells or tissue or in whole plants. As used herein, a transgenic plant also encompasses progeny of the initial transgenic plant where those progeny contain and are capable of expressing the recombinant coding sequence under the regulatory control of the plant-expressible transcription control sequences described herein. Seeds containing transgenic embryos are encompassed within this definition.

Individual plants within a population of transgenic plants that express a recombinant gene may have different levels of gene expression. The variable gene expression is due to multiple factors including multiple copies of the recombinant gene, chromatin effects, and gene suppression. Accordingly, a phenotype of the transgenic plant may be measured as a percentage of individual plants within a population. In one embodiment, greater than or equal to about 25% of the transgenic plants express the phenotype. Specifically, greater than or equal to about 50% of the transgenic plants express the phenotype. More specifically, greater than or equal to about 75% of the transgenic plants express the phenotype. The phenotype is metal resistance or arsenic resistance.

The transgenic plant is transformed with a recombinant polynucleotide or nucleic acid molecule comprising a plant arsenic resistance coding sequence operatively linked to a plant-expressible transcription regulatory sequence. Suitable plant arsenic resistance coding sequences include sequences that are homologous to a plant arsenate reductase gene. Exemplary plant arsenate reductase genes include *Arabidopsis* AtACR2 (SEQ ID NO:1), rice OsACR2-1 (SEQ ID NO:2), rice OsACR2-2 (SEQ ID NO:3), *Brassica* ACR2 (SEQ ID NO:4), and *Crambe* ACR2 (SEQ ID NO:21). The transgenic plant expresses a plant arsenic resistance protein. In one embodiment, the plant arsenic resistance protein is homologous to the AtACR2 arsenate reductase. Suitable plant arsenic resistance proteins include arsenic resistance proteins from rice and *Brassica* plants. Exemplary plant arsenic resistance proteins include AtACR2 (SEQ ID NO:5), OsACR2-1 (SEQ ID NO:6), OsACR2-2 (SEQ ID NO:7), BnACR2 (SEQ ID NO:8), and CaACR2 (SEQ ID NO:22).

The present inventors have transformed plants with recombinant DNA molecules that encode a plant arsenate reductase. Transgenic plants and plant cells expressing the recombinant plant arsenate reductase gene are more resistant to arsenate than wild type control plants. In one embodiment, greater than or equal to about 25% of the transgenic plants are resistant to a concentration of arsenic that is lethal to wild type control plants. Specifically, greater than or equal to about 50%, and more specifically, greater than or equal to about 75%, of the transgenic plants are resistant to a concentration of arsenic that is lethal to wild type control plants. The transgenic plants have reduced arsenic uptake and translocation to above ground tissues. In one embodiment, the total arsenic accumulation in the above ground tissue in transgenic plant is less than or equal to about 75%; specifically, less than or equal to about 50%; and more specifically, less than or equal to about 25% of the total arsenic accumulation in the above ground tissue in wild type control plants. The reduced arsenic uptake in the transgenic plants leads to increased phosphate uptake in above ground tissue, thus enhancing plant productivity. In one embodiment, the total phosphate accumulation in the above ground tissue in the transgenic plant is greater than or equal to about 25%; specifically, greater than or equal to about 50%; and more specifically, greater than or equal to about 75% of the total phosphate accumulation in the above ground tissue in wild type control plants. In one embodiment, the total biomass accumulation in the above ground tissue in the transgenic plant is greater than or equal to about two-fold; specifically, greater than or equal to about six-fold; and more specifically, greater than or equal to about ten-fold of the total biomass accumulation in wild type control plants.

A recombinant DNA construct including a plant-expressible gene or other DNA of interest is inserted into the genome of a plant by a suitable method. Suitable methods include, for example, *Agrobacterium tumefaciens*-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of *Agrobacterium tumefaciens*. In addition to plant transformation vectors derived from the Ti or root-inducing (Ri) plasmids of *Agrobacterium*, alternative methods can be used to insert DNA constructs into plant cells. A transgenic plant can be produced by selection of transformed seeds or by selection of transformed plant cells and subsequent regeneration.

Techniques are well known to the art for the introduction of DNA into monocots as well as dicots, as are the techniques for culturing such plant tissues and regenerating those tissues. Monocots that have been successfully transformed and regenerated include wheat, corn, rye, rice and asparagus. For efficient regeneration of transgenic plants, it is desired that the plant tissue used in the transformation possess a high capacity to produce shoots. For example, Aspen stem sections have good regeneration capacity. Poplars have been successfully transformed and regenerated as have cottonwoods.

In one embodiment, a recombinant DNA, such as a transgene construct, is introduced into rice plants. Transformed rice cells are selected and regenerated into transgenic rice plants. In one embodiment, transformed rice cells are selected on media containing an appropriate antibiotic. The rice cells are induced to form a somatic embryogenic callus. The callus is treated with the appropriate reagents such as plant hormones to induce the formation of root and shoot tissue. In this manner, transgenic rice plants can be regenerated from the callus derived from transformed rice cells.

In one embodiment, the plant arsenate reductase coding sequence is subcloned under the control of the soybean plant ribulose biphosphate carboxylase (Rubisco) small subunit promoter SRS1 and the 3' nos terminator in pBluescript®. This coding sequence and promoter are previously shown to be strongly transcriptionally induced in leaves by light. Expression directed by this promoter is very low in roots. The entire chimeric gene including the SRS1 promoter, the arsenate reductase coding sequence, and the 3' nos transcription terminator sequence, is subcloned into the plant expression T-DNA binary vector pBIN19, that has the selectable kanamycin-resistance marker (NPTII). *A. thaliana* is transformed using vacuum infiltration technology, and the T1 generation seeds are screened for kanamycin resistance. Transgenic plants transformed with an isolated arsenate reductase polynucleotide are produced. In one embodiment, the plant also expresses a phytochelatin biosynthetic enzyme coding sequence, e.g., γ-ECS, PS and/or GS.

The transgenic plant optionally further comprises an isolated polynucleotide suitable for expression of a phytochelatin biosynthetic enzyme coding sequence. In another embodiment, the arsenic-resistant transgenic plants also overexpress thiol-rich peptides like glutathione and phytochelatins to further improve arsenic tolerance. Phytochelatins (PCs) are small peptides that are synthesized non-ribosomally from common amino acid precursors in a three-step enzymatic pathway. Suitable genes that encode phytochelatins include the prokaryotic gamma-glutamylcysteine synthase (γECS) and glutathione synthase (GS) genes and the eukaryotic phytochelatin synthase (PCS) genes. Exemplary phytochelatin genes include the *E. coli* γECS (GenBank Accession no. X03954; SEQ ID NO:9) and GS (GenBank Accession no. U28377; SEQ ID NO:10) genes and the PCS genes from fission yeast (*Schizosaccharomyces pombe*) (GenBank Accession no. Z68144; SEQ ID NO:11). In one embodiment, the phytochelatin biosynthetic enzyme coding sequence is greater than or equal to about 75%, 85%, 90% or 95% homologous with a sequence selected from the group consisting of SEQ ID NO:9, SEQ ID NO:10, and SEQ ID NO:11, wherein the phytochelatin biosynthetic enzyme coding sequence has phytochelatin biosynthesis activity. Plants that co-express a phytochelatin synthetic gene such as γECS, GS and PCS together with an arsenate reductase gene are further improved in metal resistance. In one embodiment, phytochelatin biosynthetic genes are overexpressed in roots. Without being bound by theory, it is believed that by overexpressing phytochelatin biosynthetic genes in roots, the thiol-rich peptides will bind arsenite generated in roots and thus improve arsenic tolerance and further prevent the movement of arsenic to the aboveground tissues.

In one embodiment, the levels of PC pathway intermediates (gamma-EC, GSH and PC) are expressed at a level in excess of 1% of the total cell protein. In this example, three vector systems are used for all three PC synthesizing enzymes in order to compare their activity and to avoid potential co-suppression problems. For strong constitutive expression and as an alternative promoter to the CaMV 35S promoter, a novel actin promoter expression vector, ACT2pt was developed. The ACT2pt comprises the promoter (p) and terminator (t) from the constitutive ACT2 gene. In controlled experiments with 30 independent ACT2pt/reporter lines and 30 independent 35Sp/reporter lines, the ACT2pt vector gives about 5-10 times higher levels of reporter expression than the 35Sp vector. In several independent experiments using the ACT2pt vector, co-suppression of the endogenous ACT2 gene or the transgene was not observed, even when multiple copies are present. While a plant with low levels of ACT2pt driven expression was not obtained, approximately 10-20% of the 35Sp plants had no detectable reporter expression. Furthermore, the lowest ACT2pt plants are equivalent to the highest 35Sp plants. This apparent insensitivity to cosuppression offers a significant advantage in the multigene strategy being used.

In one embodiment, the transgenic plants are grown (e.g., on soil) and harvested. The soil may contain levels of arsenic that is toxic to wild type plants. In one embodiment, above ground tissue is harvested separately from below ground tissue. Suitable above ground tissues include shoots, stems, leaves, flowers, grain, and seed. Exemplary below ground tissues include roots and root hairs. In one embodiment, whole plants are harvested and the above ground tissue is subsequently separated from the below ground tissue. In one embodiment, plant tissue that contains low levels of arsenic is harvested separately from plant tissue that contains high levels of arsenic. Harvesting plant tissue optionally comprises separating plant tissue having reduced metal or metal ion accumulation from plant tissue having increased metal or metal ion accumulation. The plant tissue that contains low levels of arsenic can be harvested separately on the field or can be separated from other plant tissue after whole plants are harvested.

In one embodiment, the transgenic plant also expresses a thiol-rich peptide. In one embodiment, the polynucleotides encoding thiol-lich peptides are modified by PCR to comprise appropriate sites for cloning to make in-frame translational fusions with actin and SRS1 light regulated promoters. In one embodiment, the polynucleotides are modified for detection in E. coli and plants. Monoclonal antibodies specific to AtACR2, γECS, GS, and PCS (fission yeast) proteins have been generated to monitor protein expression. The Arabidopsis PCS protein was tagged with an HA (hemagglutinin) epitope to allow monitoring with a commercially available HA-specific antibody. All four proteins confer increased metal tolerance to E. coli, when expressed under the control of the lac promoter in pBluescript® vectors. In one embodiment, all four genes are derived from plants including, for example, Arabidopsis and rice. Without being bound by theory, it is believed that thiol-rich peptides such as glutathione and phytochelatins, bind arsenic and contribute to arsenic tolerance and accumulation. It is believed that the GS-As and PC-As complexes are pumped into vacuoles for storage, thus improving arsenic tolerance.

The plant arsenate reductase enzyme uses glutathione as a hydrogen/electron donor in the electrochemical reduction of the oxyanion arsenate to the oxyanion arsenite. While arsenate is a phosphate analogue, arsenite is chemically very different, being a highly reactive species with strong affinity toward thiol groups such as those in GSH, PCs and metallothioneins (MTs). Converting arsenate to arsenite favors the trapping of arsenic in thiol complexes. In one embodiment, the transgenic plants overexpress a plant arsenate reductase and a thiol-rich peptide to synergistically improve arsenic resistance. The overexpression of the plant arsenate reductase improves the arsenate reduction capacity of the plant cells while the overexpression of the thiol-rich peptides provide thiol sinks for the arsenite produced by the arsenate reductase. For example, the transgenic plant co-overexpresses heterologous PC synthetic genes and plant arsenate reductase. In one embodiment, the transgenic plant overexpresses the heterologous PC synthetic genes and plant arsenate reductase in the above ground tissue including, for example, leaves, shoots, stems, and seeds.

In one embodiment, transgenic plants are transformed with vectors that provide overexpression of thiol-rich peptides. For example, the ACT2pt vector has been used to drive exceptionally high levels of constitutive transgenic expression of GS throughout the plant. The ACT2pt vector may further contain intron (IVSL) that enhances expression 20-fold. The ACT2 poly(A) region (Act2t) ensures efficient transcription termination, and it contains multiple polyadenylation sites.

The following examples are provided for illustrative proposes and are not intended to limit the scope of the invention as claimed herein. Any variations in the exemplified compositions and methods, that occur to the skilled artisan, are intended to fall within the scope of the present invention.

EXAMPLES

Strains and Plasmids

Escherichia coli strain AW10 contains plasmid pArsAB200 that has the arsA and arsB genes, E. coli JM109 contains plasmid pAlter-C that bears the arsC gene, and E. coli RW3110 is a strain in that a Zn (II)/Cd (II) pump gene termed as zntA is knocked out, as described previously. The pBluescript® SK (−) plasmid (Stratagene, La Jolla, Calif.) and promoterless binary vector pBIN19 (Clontech, Palo Alto, Calif.), designed for expressing genes under promoter of interest by Agrobacterium-mediated transformations, are obtained commercially.

Example 1

Cloning ACR2 Genes

Various plant databases were searched for genes encoding amino acid sequence homologs of the previously described E. coli ArsC and Saccharomyces cerevisiae ScACR2 arsenate reductases. Sequences that are the likely plant homologs of the ScAcr2p protein sequence were identified, but nothing related in overall sequence to E. coli ArsC. The gene for the putative A. thaliana (Columbia ecotype) homolog, which was designated the AtACR2 gene, is located on chromosome V (locus At5g03455) and is composed of three exons. The predicted ORF within AtACR2 is 399 bp (SEQ ID NO:1), encoding a protein of 132 aa with a molecular mass of 14.5 kDa and an estimated basic isoelectric point of pI=8.9 (SEQ ID NO:5). In pairwise comparisons, AtACR2 shares 33% amino acid sequence identity and 42% overall similarity with the 130-residue ScAcr2 protein and 32% identity and 40% overall similarity with the 127-residue Leishmania LmACR2 protein. AtACR2 has the signature amino acid motif ($HCX_5R$) associated with arsenate reductase activity, which is located within the predicted 9-aa active site.

The AtACR2 sequence was cloned into BamHI-XhoI replacement region of pBluescript® II SK (Stratagene) to make a bacterial expression plasmid pACR2/BS. This construct was transformed into the two E. coli strains AW10 (pArsAB200) and AW3110. The same E. coli strains were also transformed with empty plasmid pBS to serve as negative controls.

For plant expression, the AtACR2 sequence was subcloned under the regulatory control of the 1.5 kb Rubisco small subunit SRS1 promoter (GenBank Accession No. X58684; SEQ ID NO. 14) or the Arabidopsis actin ACT2 promoter and the nopaline synthase (nos) 3' terminator to create pSRS1p/

AtACR2/nos and pACT2p/AtACR2/nos respectively. The entire cassette containing the promoter, AtACR2 coding sequence and nos 3' terminator, was subcloned into the *Agrobacterium* pBIN19 Ti vector for transformation into plants.

Figure 2:
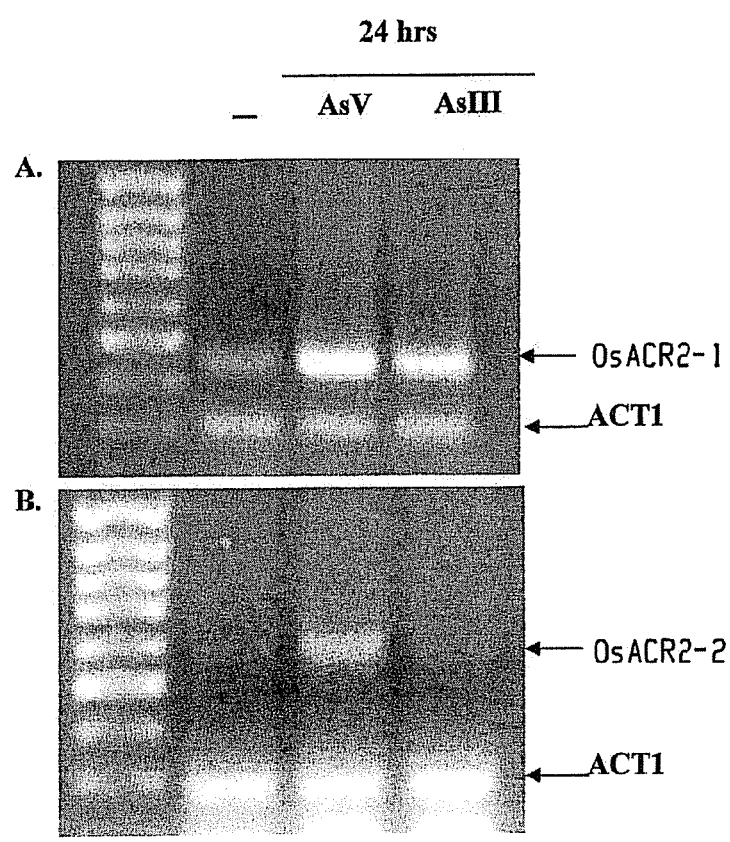
FIG. 2 shows the expression of OsACR cDNAs in rice in response to arsenic.

Two homologs from rice (*Oryza sativa* (japonica cultivar)) were cloned using cDNA libraries made from both shoot and root tissues. The rice homologs are designated OsACR2-1 and OsACR2-2. Based on the DNA sequences, the full length OsACR2-1 protein is predicted to be 137 aa long with 60% identity over 132 aa of the predicted AtACR2 protein. The full length OsACR2-2 protein is predicted to be 130 aa long with 63% identity over 126 aa of the predicted AtACR2 protein. By RT-PCR analysis, the OsACR2-1 and OsACR2-2 genes are expressed in both root and shoot tissues. FIG. 1. Both genes are also further induced in response to arsenic exposure. FIG. 2.

The 132-codon AtACR2 cDNA was amplified by PCR using a sense primer, 5'-TACGTCGGATCCTAAGGAG-GATAGACCATGGCGATGGCGAGAAGCAT-3', (SEQ ID NO:15), and an antisense primer, 5'-TAGGTCCTCGAGT-TAGGCGCAATCGCCCTTGCAAGGAACCTCTGCACA-3', (SEQ ID NO:16), from an *Arabidopsis* flower cDNA library. PCR was carried out for 45 cycles with denaturing, annealing and extending temperatures and times of 94° C. for 1 min, 48° C. for 1 min, and 72° C. for 1 min.

The rice OsACR2 genes were amplified and cloned from cDNA libraries generated from rice shoot and root tissues. The rice shoot and root cDNA libraries were made after 24 hour induction with 300 μM sodium arsenate and 100 μM sodium arsenite. The 137 amino acid codon OsACR2-1 was PCR amplified using sense primer, 5'-TACGTCGGATC-CAGGAGGTAGACCATGGCGCGGAGCGT-GTCGTACGTGTCGGCGGCGAAGCTCCTGGCAAT-3', (SEQ ID NO:17), and the antisense primer, 5'-TAGCT-GCTCGAGAAGCTTTTACAACTCAGGTTCTTCAGGT-3', (SEQ ID NO:18). Similarly, the 130 amino acid codon OsACR2-2 cDNA was amplified by PCR using sense primer, 5'-TACGTCGAATTCAGGAGGTAGACCATG-GCGAGGGGCGTCTCCTACGTTT-3', (SEQ ID NO:19), and an antisense primer, 5'-TAGCTGCTC-GAGAAGCTTTCAAGAGCACACACCCTTGCAA-3', (SEQ ID NO:20). The PCR was carried out as 1 cycle at 94° C. for 5 minutes followed by 35 cycles with denaturing, annealing and extending temperatures and times of 94° C. for 45 sec, 52° C. for 1 minutes and 72° C. for 45 seconds with an additional extension cycle of 72° C. for 10 minutes.

A homologous nucleic acid sequence was identified in clone BN25041G09 from *Brassica napus* and designated BnACR2. The *Brassica* BnACR2 gene was amplified and cloned from cDNA libraries generated from *Brassica napus* shoot and root tissues. The *Brassica* shoot and root cDNA libraries were made after 24 h induction with 150 micromolar sodium arsenate and 40 micromolar sodium arsenite. The 132-codon BnACR2 cDNA was amplified by PCR using sense primer, 5'-TACGTCGGATCCAGGAGGTAGAC-CATGGCGGCGAGAAGCATCTCT-3' (SEQ ID NO:23) and antisense primer, 5'-TAGCTGCTCGAGAAGCTTT-TAGGTGCAGTCGCCCTTGCAA-3' (SEQ ID NO:24). The PCR was carried out as 1 cycle at 94° C. for 5 min followed by 35 cycles with denaturing, annealing and extending steps at 94° C. for 45 sec, 52° C. for 1 min and 72° C. for 45 sec, respectively, with an additional step for extension at 72° C. for 10 min. The PCR amplified BnACR2 gene was cloned in pBluescriptII® SK (Stratagene) using BamHI-XhoI restriction enzymes.

The predicted protein sequence for the BnACR2 protein is MAARSISYITSTQLLPLHRRPNIAIID-VRDEERNYDGHIAGSLHYASGSFEDRIS HLVQNVKD-KDTLVFHCALSQVRGPTCARRLVNYLDE-KKQETGIKNIMILERG FNGWEAAGKPVCRCADVPCKGDCT (SEQ ID NO:8). The predicted BnACR2 protein sequence is over 94% identical to the AtACR2 protein.

A homologous nucleic acid sequence was identified in *Crambe abyssinica* designated CaACR2 (SEQ ID NO:21). The *Crambe* CaACR2 gene was amplified and cloned from cDNA libraries generated from *Crambe abyssinica* shoot and root tissues. The *Crambe* shoot and root cDNA libraries were made after 24 h induction with 150 micromolar sodium arsenate and 40 micromolar sodium arsenite. The 132-codon CaACR2 cDNA was amplified by PCR using sense primer, 5'-TACGTCGGATCCAGGAGGTAGACCATG-GCGGCGAGAAGCATCTCT-3' (SEQ ID NO:25) and antisense primer, 5'-TAGCTGCTCGAGAAGCTTTTAGGTG-CAGTCGCCCTTGCAA-3' (SEQ ID NO:26). The PCR was carried out as 1 cycle at 94° C. for 5 min followed by 35 cycles with denaturing, annealing and extending steps at 94° C. for 45 sec, 52° C. for 1 min and 72° C. for 45 sec, respectively, with an additional step for extension at 72° C. for 10 min. The PCR amplified CaACR2 gene was cloned in pBluescriptII SK (Stratagene) using BamHI-XhoI restriction enzymes.

Figure 3:
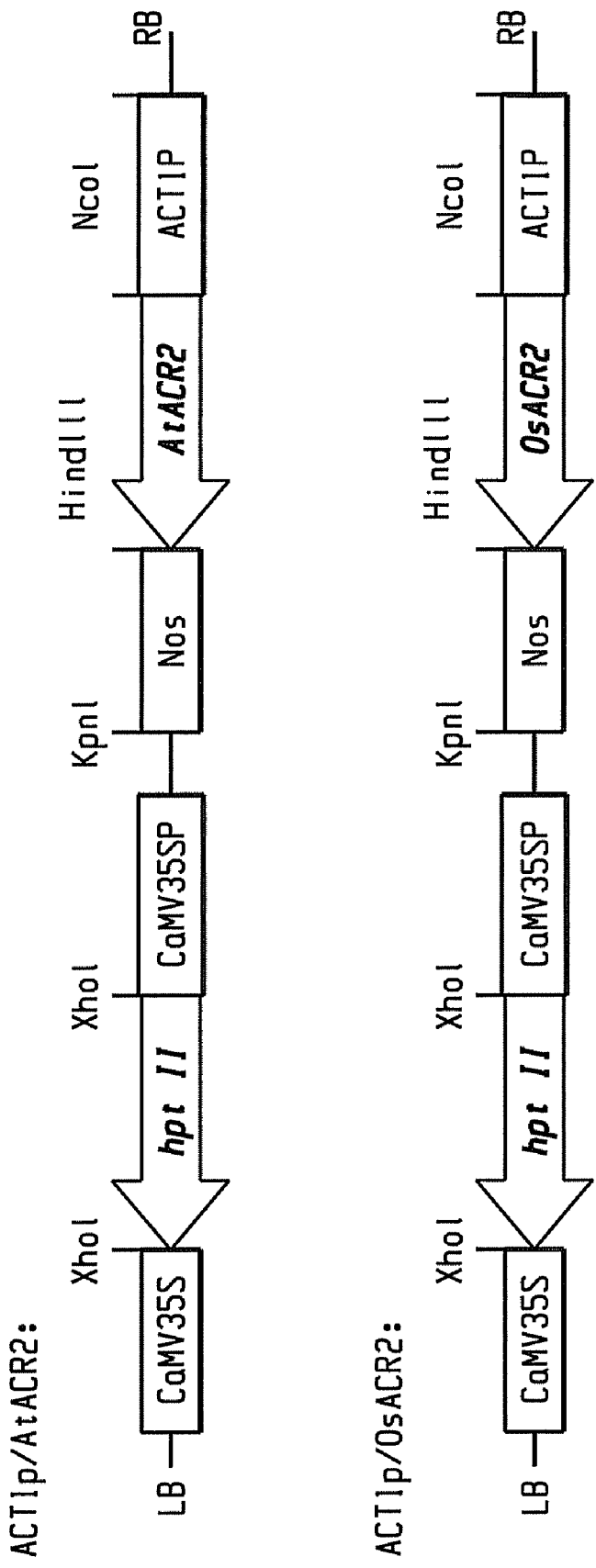
FIG. 3 shows a schematic diagram of vector constructs used to transform plants.

The PCR amplified OsACR2-1 (SEQ ID NO:2), OsACR2-2 (SEQ ID NO:3), BnACR2 (SEQ ID NO:4), and CaACR2 (SEQ ID NO:21) polynucleotides were cloned in pBluescript® II SK (Stratagene) using EcoRI-XhoI and BamHI-XhoI combination of restriction enzymes, respectively. For overexpression of AtACR2 and OsACR2 in plants, the EcoRI-XhoI and BamHI-XhoI fragments, respectively, of these genes were cloned under an expression vector pACT1p/NOSt. The expression vector pACT1p/NOSt has rice ACT1 gene promoter and NOS gene terminator. The KpnI-SacI fragment containing the entire gene cassette (ACT1p/OsACR2/NOSt) was taken out from pACT1p/NOSt and subcloned into pCambia binary vector for transformation into *Agrobacterium* strain LBA4404. A map of the constructs is shown in FIG. 3 with the left and right borders of the T-DNA labeled LB and RB, respectively.

Example 2

Cloning γ-ECS, GS, and PS for Bacterial Expression

The γ-ECS (GenBank Accession no. X03954; SEQ ID NO:9) and GS (GenBank Accession no. 28377; SEQ ID NO:10) genes were amplified by PCR, using synthetic primers, from genomic DNA of *E. coli* SK1592. The fission yeast *Schizosaccharomyces pombe* PS gene (GenBank Accession no. Z68144; SEQ ID NO:11) was amplified from a plasmid PsPC/YES clone provided by Julian Schroeder (University of California, San Diego, Calif.). The two oligonucleotide primers for each gene added synthetic flanking sequences necessary for cloning and bacterial expression. The sense primers contained restriction endonuclease cloning sites XhoI and NcoI, a TAA stop codon, and bacterial translation signals. The antisense primers contained cloning sites BamHI and HindIII. The PCR products encoding all three genes were cloned first into the XhoI/BamHI replacement region of pBluescript® KS(II) (Stratagene, La Jolla, Calif.) and electroporated into *E. coli* strain Top10F (Invitrogen, Carlsbad, Calif.). Sequencing confirmed the fidelity of the amplified coding sequences. To express higher levels of protein, the three genes were subcloned into the NdeI (blunt end)/BamHI replacement region of the expression vector pET15b (Novagen, Madison, Wis.) using post-ligation-digestion with XhoI to select against the parent pET15b vector. These plasmids were expressed in *E. coli* strain BL121 (Novagen) as per the manufacturer's instructions.

Example 3

Complementation of *E. coli* ars mutants with plant ACR2 cDNAs

Assays of the plant arsenate reductase gene activity were performed in *E. coli* arsC mutant backgrounds. Sodium arsenate and arsenic chloride (Sigma Chemical Co., St. Louis, Mo.) solutions were prepared in sterile water. Because of the extreme toxicity membrane permeability of these chemicals, dry stocks, and stock solutions were handled using protective clothing, eye protection, and double layers of gloves. All metal ion-sensitivity filter disk assays were performed in the presence of ampicillin to maintain the pBS II SKplasmid. Approximately $2 \times 10^8$ cells carrying the lac-regulated arsC sequence were plated in top agar on LB medium containing IPTG (1 mM final concentration) and appropriate antibiotics. 5 or 10 μl aliquots of metal ion solution (250 mM $As_2O_5$) was pipetted onto 6 mm diameter sterile 3 mm Whatman paper disks, that were placed on solidified top agar containing the strains of interest. The plates were incubated overnight at 37° C., and the zones of growth inhibition are then measured.

Figure 4:
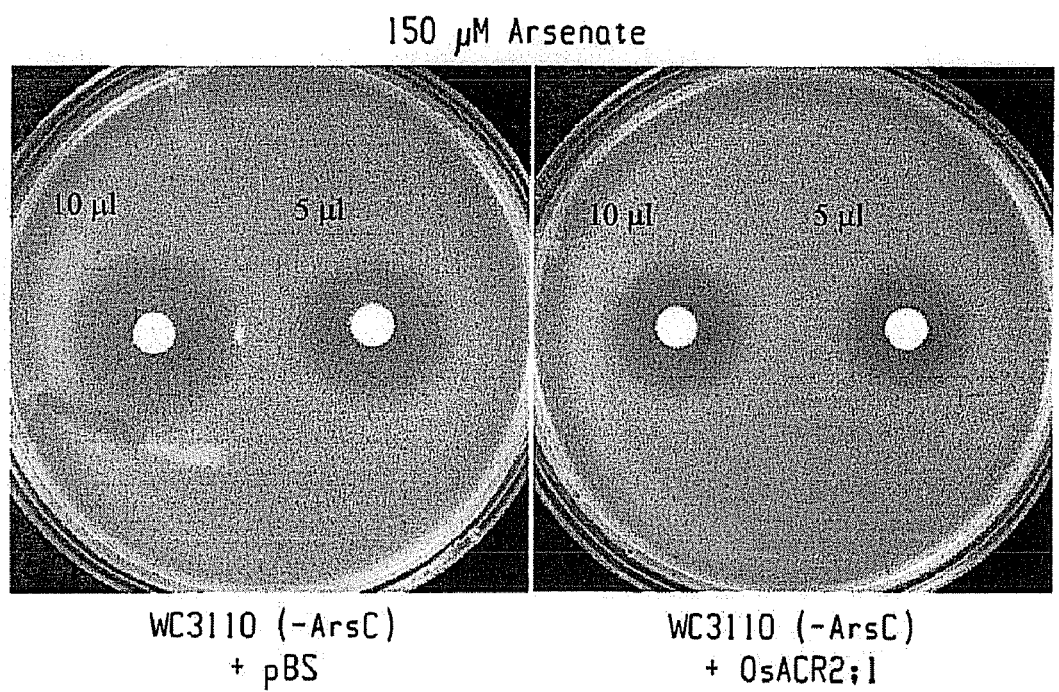
FIG. 4 shows functional complementation of bacterial ars mutants with rice cDNAs.

In order to prove that OsACR2 cDNAs encode functional arsenate reductases, we carried out the complementation assays in *E. coli* strains lacking endogenous arsenate reductase, ArsC. The *E. coli* strains lacking only ArsC are sensitive to AsV as these strains cannot reduce AsV to AsIII and thus exhibit AsV sensitivity. In these complementation assays, we overexpressed the OsACR2-1 (SEQ ID NO:6) and OsACR2-2 (SEQ ID NO:7)proteins in *E. coli* strain WC3110, which lacks ArsC but has an intact ArsAB export pump, and analyzed the cells on media containing AsV for resistance/sensitive phenotype. The *E. coli* strain WC3110 transformed with either empty vector pBS or pBS containing a rice OsACR2 cDNA were grown on LB agar plates. Two sterilized 3 mm round filter discs were placed on each plate and 5 and 10 ml of 250 mM arsenate was pipetted on each disc. The bacterial ArsC was used as a positive control and empty pBS vector as a negative control. The plates were incubated overnight at 37° C. The zone of clearance was measured. The size of the zone of clearance is directly related with the resistance or sensitivity of the strain such that the smaller the size of zone, the more resistant the cells are, and vice versa. Both rice putative arsenate reductases, OsACR2-1 and OsACR2-2, complemented ArsC-deficient phenotype and showed significant resistance to arsenate. The zone of inhibition was smaller in cells expressing rice OsACR2-1 and OsACR2-2 as shown in FIG. 4.

In addition, the ability of the 132-residue AtACR2 polypeptide (SEQ ID NO:5) to complement the arsenic sensitivity of *E. coli* strain AW10, which is defective in arsenate reductase activity, was tested. In this strain, the entire chromosomal ars operon, including the arsenate reductase gene arsC, was deleted (Δars), but the arsA and arsB genes encoding the bacterial arsenite efflux pump were carried on a plasmid (pArsAB200). Expression of the pump confers resistance to arsenite, but the cells remain sensitive to arsenate, allowing complementation by heterologous arsenate reductases.

The AtACR2 gene was cloned under control of a bacterial promoter to make pAtACR2/BS. Strain AW10 pArsAB200 was transformed with plasmid pAtACR2/BS and also with an empty pBS vector or pNA1, which expresses bacterial arsC, as negative and positive controls, respectively. A wild-type W3110 strain with an intact ars operon was also included as a positive control. The growth kinetics of these strains grown on liquid media with a fixed concentration of arsenate (250 micromolar), after induction by the lac inducer isopropyl β-D-thiogalactoside, were determined. Strains were grown overnight at 37° C. in Luria-Bertani medium (LB) with appropriate antibiotics and isopropyl β-D-thiogalactoside (IPTG). For the time-dependent liquid growth curve assays, the cultures were diluted 100-fold into half-strength LB and grown for various time periods in the presence of final concentrations of 100 mg/liter ampicillin, 50 mg/liter kanamycin, 1 millimolar IPTG, and 250 micromolar sodium arsenate. Cell density was measured as Klett units at 1-h intervals.

Strain AW10 with pArsAB200 and pBS was sensitive to arsenate, as expected, because it cannot enzymatically reduce arsenate and make arsenite available to the export pump. The AtACR2 sequence in pAtACR2/BS complemented this phenotype and showed significant resistance to arsenate that was almost equivalent to that conferred by expression of the bacterial ArsC protein from pNA1. Neither strain grew quite as well as the wild-type control (W3110+pBS). Resistance to arsenate conferred by pACR2/BS is most simply interpreted as caused by the reduction of arsenate to arsenite by ACR2, with subsequent extrusion of arsenite out of the cells by the arsenite export pump. Attempts to complement yeast ScAcr2 mutants with AtACR2 were unsuccessful. This result was somewhat unexpected since the AtACR2 protein sequence shows some similarity with the eukaryotic ScAcr2p protein sequence, but does not show a high degree of similarity in overall sequence to the prokaryotic ArsC protein.

Example 4

Construction of Transgenic *Arabidopsis* Plants

Plasmid pBIN/AtACR2, carrying the chimeric plant arsenate reductase gene (SRS1P:AtACR2:nos3'), was electroporated into cells of the C58 *Agrobacterium tumefaciens* strain (GIBCO/BRL, Gaithersburg, Md.). Transformants were verified by using Southern blotting and/or PCR and cultured in YEP medium (10 g/liter Bacto peptone (Difco, Detroit, Mich.)/10 g/liter yeast extract/5 g/liter NaCl) in the presence of streptomycin and kanamycin to maintain the T-DNA and pBIN19 plasmids, respectively. Wild-type *A. thaliana* (ecotype Columbia) plants were transformed with the recombinant *A. tumefaciens* strains using the vacuum infiltration procedure.

Example 5

Construction of Transgenic *Japonica* Rice Plants

Mature *japonica* cv. Nipponbare rice seeds were dehusked, surface sterilized and placed onto callus induction medium. The callus tissue derived from the mature embryo was then used as the starting material for transformation. *Agrobacterium tumefaciens* strain LBA4404 contained the standard binary vector pCAMBIA1300 harboring the AtACR2 gene under rice ACT1 promoter and nos terminator. The plant selectable marker gene hygromycin phosphotransferase (hpt) is driven by the cauliflower mosaic virus (CaMV) promoter.

Media:
Callus induction medium: 30 g/L sucrose, N6 salts and vitamins, 1 g/L casein hydrolysate, 0.5 g/L L-proline, 0.5 g/L glutamine, 2 mg/L 2,4-D and 4 g/L gelrite (pH 5.8).

Regeneration medium: 30 g/L sucrose, MS salts and vitamins, 1 g/L casein hydrolysate, 2 mg/L BAP, 0.5 mg/L NAA and 4 g/L gelrite (pH 5.8).

Rooting and shoot multiplication medium: 30 g/L sucrose, MS salts and vitamins and 4 g/L gelrite (pH 5.8).

Infection medium: 68.4 g/L sucrose, 36 g/L glucose, N6 salts and vitamins, 1 g/L casein hydrolysate, 0.5 g/L L-proline, 0.5 g/L glutamine, 2 mg/L 2,4-D (pH 5.2). Acetosyringone (AS 100 µM) is added just prior to use.

Co-cultivation medium: 30 g/L sucrose, 10 g/L glucose, N6 salts and vitamins, 1 g/L casein hydrolysate, 0.5 g/L L-proline, 0.5 g/L glutamine, 2 mg/L 2,4-D, 4 g/L gelrite (pH 5.8). Acetosyringone (AS 100 µM) is added just prior to use.

Selection medium I: 30 g/L sucrose, N6 salts and vitamins, 1 g/L casein hydrolysate, 0.5 g/L L-proline, 0.5 g/L glutamine, 2 mg/L 2,4-D and 4 g/L gelrite (pH 5.8). 300 mg/L cefotaxime and 50 mg/L hygromycin are added to this medium after autoclaving.

Selection medium II: 30 g/L sucrose, MS salts and vitamins, 1 g/L casein hydrolysate, 2 mg/L BAP, 0.5 mg/L NAA and 4 g/L gelrite (pH 5.8). 200 mg/L cefotaxime and 50 mg/L hygromycin are added to this medium after autoclaving.

Callus Induction

Rice seeds were dehusked, pre-rinsed with 70% ethanol for 2 minutes and washed with twice with sterile water. The seeds were then soaked in 0.1% $HgCl_2$ in a 125 ml sterile conical flask and placed on a shaker for 30 minutes. The seeds were washed 5 times with sterile water, dried on sterile filter paper. The surfaced sterilized seeds were then kept on callus induction medium (15 seeds per plate) and incubated in light at 25° C. After 2-3 weeks, developing callus was visible on the scutellum of the mature seed. Calli were sub-cultured to fresh induction medium and allowed to proliferate.

*Agrobacterium infection*: A single colony of *Agrobacterium tumefaciens* strain LBA4404 containing the gene cassette was grown in 5 ml YEP medium (5 g/L yeast extract, 10 g/L peptone, 5 g/L NaCl) containing 50 mg/L rifampicin, 100 mg/L kanamycin and used as inoculum for 50 ml overnight culture. Overnight grown *Agrobacterium* culture was adjusted to OD600 0.5 with infection medium. The liquid infection medium was supplemented with 100 µM acetosyringone (AS). The calli were infected with this medium for 1 hour in conical flasks on a shaker (low setting).

After infection the bacterial suspension was removed. The calli were blotted dry on sterile filter paper and placed on co-cultivation medium. The calli were co-cultivated in dark at 25° C. for 3 days.

The infected calli were washed 5 times with sterile water, blotted dry on sterile filter paper and transferred to selection medium containing 300 mg/L cefotaxime and 50 mg/L hygromycin. Election plates were wrapped with parafilm and placed in the light at 25° C. The tissue were subcultured onto fresh selection medium every two weeks. After 6-8 weeks selection the actively growing callus was distinguished from the brown non-transformed tissue.

Figure 5:
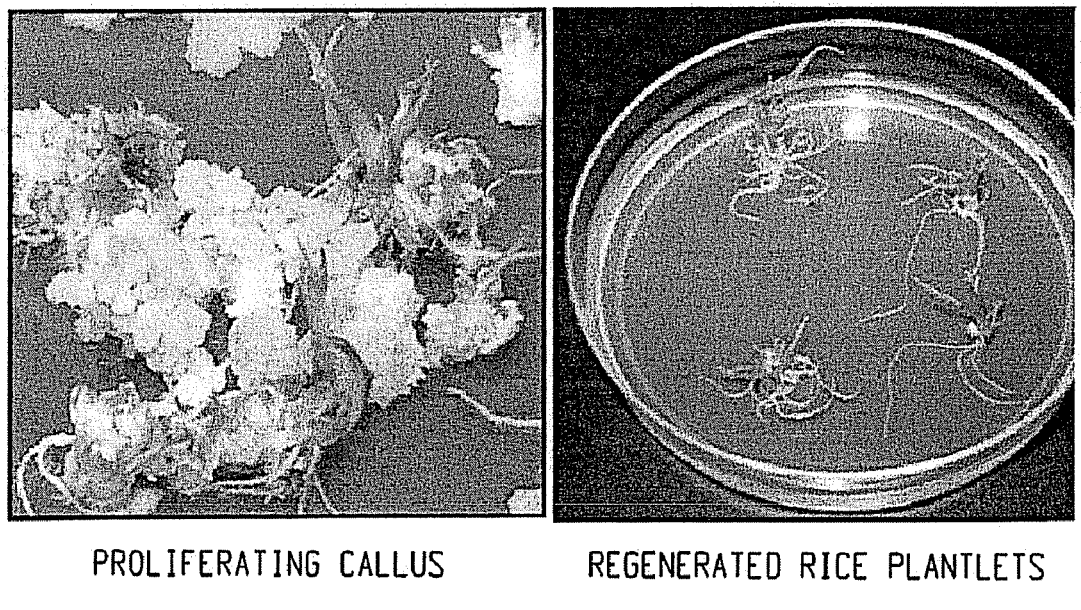
FIG. 5 shows rice calli and regenerated rice plantlets.

The white proliferating calli in presence of hygromycin were transferred to regeneration medium I (in light at 25° C.). After 2-3 weeks the regenerated shoot buds were transferred to regeneration medium II (in light at 25° C.). FIG. 5 shows proliferating calli and regenerated plantlets. The rooted plants were transferred to soil and grown in green house.

Example 6

Germination, Growth and Metal Analysis of Transgenic *Arabidopsis*

Wild-type (Columbia) and transgenic *Arabidopsis* seeds were sterilized by rinsing in 70% ethanol for 1 minute, then in 30% CLOROX™ bleach (5.25% sodium hypochlorite) for 30 minutes with frequent shaking, followed by 4 rinses in sterile water. Sterilized seeds were sown on one half strength MS medium containing 30 g/liter sucrose, 0.8% PHYTAGAR (purified agar) (GIBCO/BRL, Invitrogen, Carlsbad, Calif.), pH 5.7 and 75 or 150 micromolar sodium arsenate (~6 and 12 ppm elemental arsenic). The seeds plated on media were vernalized at 4° C. for at least 25 hours. Seedlings were grown at 22° C. with a daily regime of 16 hours light/8 hours darkness. Shoots and roots of three-week old individual seedlings were harvested separately, rinsed with sterile water, dry-blotted, weighed and root length was measured. Harvested tissues are frozen in liquid nitrogen, lyophilized and stored at −80° C. until needed.

Plant samples were dried at 70° C. for 48 hours, ground to a fine powder in 15 ml tubes with a homogenizer, and digested in a mixture of nitric and perchloric acids (7:1 vol/vol) with shaking for 24 hours. The digested samples were centrifuged and the clear supernatant was analyzed for total elemental analysis using Inductively-coupled Plasma mass spectroscopy (ICP-MS). Certified National Institute of Standard and Technology plant standards (peach leaves) were digested and analyzed as well. In addition, reagent blanks and the internal standards were used, where appropriate, to insure accuracy and precision in the analysis.

Example 7

Analysis of RNAi Knockdown ACR2 Lines in *Arabidopsis*

RNAi was used to knock down ACR2 expression in *Arabidopsis* plants. The RNAi gene construct AtACR2Ri targeted approximately 200 bp of the 3' UTR of the AtACR2 transcript for degradation and was expressed under the control of a constitutive promoter in transgenic *Arabidopsis* plants. Six RNAi lines with single transgene insertions were designated as Ri25, Ri27, Ri32, Ri35, Ri37, and Ri39. The T2 generation transgenic seeds and plants did not show any phenotypic differences from nontransformed *Arabidopsis* when grown on regular plant media or soil.

Antibodies produced against the plant arsenate reductase protein were used to analyze the arsenate reductase expression in the transgenic lines at the protein level. Immunoblot (Western blot) analysis of root tissues by using an AtACR2-specific antibody showed a significant decrease in the levels of the 14.5-kDa ACR2 protein in all of the knockdown RNAi lines compared with wild type plants. Specifically, the RNAi lines contained about 2% to about 50% of wild type protein levels. The levels of the 110-kDa phosphoenolpyruvate (PEP) carboxylase (pAbPEPC) polypeptide served as a loading and protein transfer control. AtACR2 protein was also detected in shoot tissues of wild type plants, although the levels of protein were lower than in roots. Microarray analyses of *Arabidopsis* transcript levels suggested that AtACR2 mRNA was constitutively expressed at low levels in all plant organs. *Arabidopsis* wild type and the six independent AtACR2Ri knockdown lines assayed by Western blotting were tested for arsenic sensitivity by germination on medium containing various arsenate concentrations, as shown for line ACR2Ri39.

Concentrations of arsenate of 100 micromolar or less had minimal effects on the growth of either wild type plants or the RNAi lines. The RNAi lines were significantly more sensitive to arsenate in comparison with wild type at 150 micromolar arsenate. The ACR2Ri lines germinated as well as wild type, but, after 3 weeks of growth, the knockdown plants attained 5- to 6-fold less fresh weight than wild type controls. There was no significant difference in fresh weight between transgenic lines and wild type plants when grown on media not supplemented with arsenate.

If the AtACR2Ri knockdown lines were arsenic sensitive because of a lack of arsenate reduction to arsenite, then there should be no difference in their sensitivity to arsenite as compared to wild type plants. Both transgenic and wild type plants were grown on a concentration of arsenite (25 micromolar As(III)) that significantly inhibited the growth of wild type. Both wild type and the AtACR2 RNAi knockdown lines were equally sensitive to arsenite, and there were no obvious phenotypic differences. These results are consistent with AtACR2 functioning as an arsenate reductase. Without being bound by any particular theory, it is predicted that arsenate is the most mobile form of arsenic in the majority of plant species and that arsenite stays trapped in roots. Thus, if these RNAi lines enzymatically reduced arsenate less efficiently than wild type because of lower AtACR2 enzyme levels, they should transport more arsenate to shoots. The AtACR2Ri knockdown lines showed significantly higher concentrations of arsenic in their shoots and retained slightly less arsenic in their roots than wild type when grown on 100 micromolar arsenate. At this concentration of toxicant, the RNAi lines were not significantly inhibited in growth relative to wild type.

Quantitative assays showed that these RNAi knockdown lines accumulated 10- to 16-fold more arsenic in shoots (350-500 ppm arsenic) compared with wild type controls, which accumulated only 30 ppm arsenic. In several repetitions of this experiment with 75 and 100 micromolar arsenate in the medium, all of the RNAi lines tested accumulated between 6 and 20 times higher levels of arsenic than the wild type. Whereas wild type plants have shoot-arsenic concentrations that were only 1% of their root levels, the RNAi lines have shoot concentrations that were approxinately 25% of their root levels. Clearly, AtACR2 activity plays a significant role in blocking long-distance arsenic transport and accumulation in wild type plants. When plants were grown with 25 micromolar arsenite in the medium, there was no difference in the arsenic accumulation of the RNAi lines. These results also suggest that the substrate forAtACR2 protein is arsenate and not arsenite and that blocking AtACR2 function enhances arsenate transport from roots to shoots but does not affect endogenous arsenite uptake and transport.

The accumulation of total phosphorus in plants grown with the normal amount of phosphate (625 micromolar) or in half-strength MS medium with 100 micromolar arsenate was analyzed. The AtACR2 knockdown plants accumulated 2- to 3-fold less phosphorus in shoots compared with wild type plants in response to arsenate exposure, and some lines retained slightly less phosphorus in roots. When grown with 25 micromolar arsenite in the medium, there was no difference between phosphorus accumulation in the wild type and RNAi lines. When no arsenate was added to growth media, there was again no difference in phosphorus accumulation between wild type and the AtACR2-deficient lines, with all lines accumulating about 8,000 ppm phosphorus in shoots. Plant lines AtACR2Ri25 and AtACR2Ri32, which had only moderate reductions in AtACR2 protein levels compared with the other four lines examined, showed only slight differences from wild type in the root accumulation of arsenic and phosphorus. The AtACR2Ri25 line also showed less accumulation of arsenic in shoots than the other lines, a finding that was consistent with its moderate RNAi phenotype. Further experimentation would be necessary to explain why line AtACR2Ri32 accumulated as much arsenic in shoots as the other stronger epialleles with less AtACR2 protein.

Example 8

Analysis of Transgenic *Arabidopsis* Lines

Figure 6:
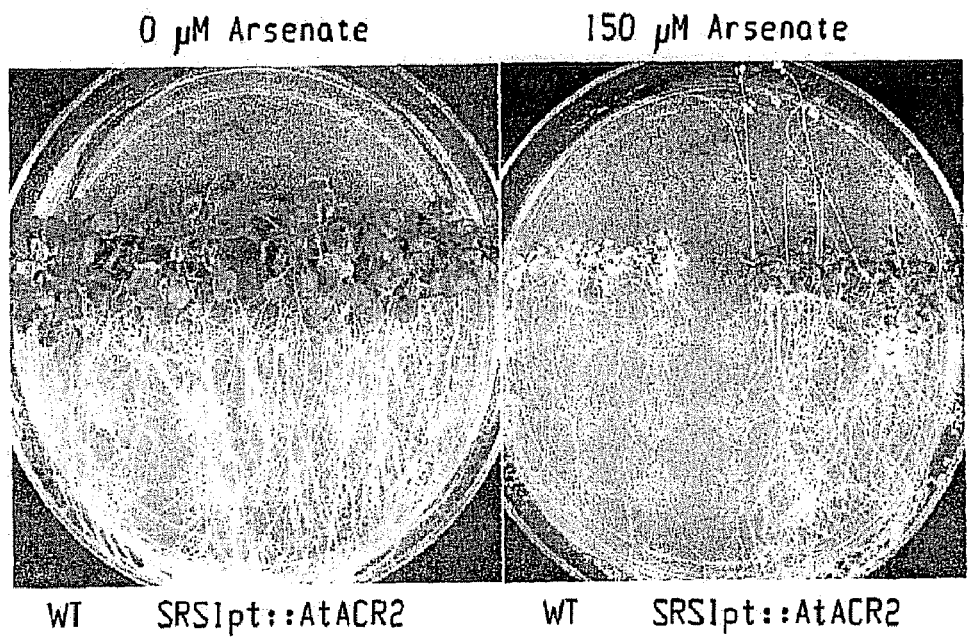
FIG. 6 shows increased arsenic resistance and biomass in transgenic *Arabidopsis* lines that overexpress AtACR2.
Figure 7:
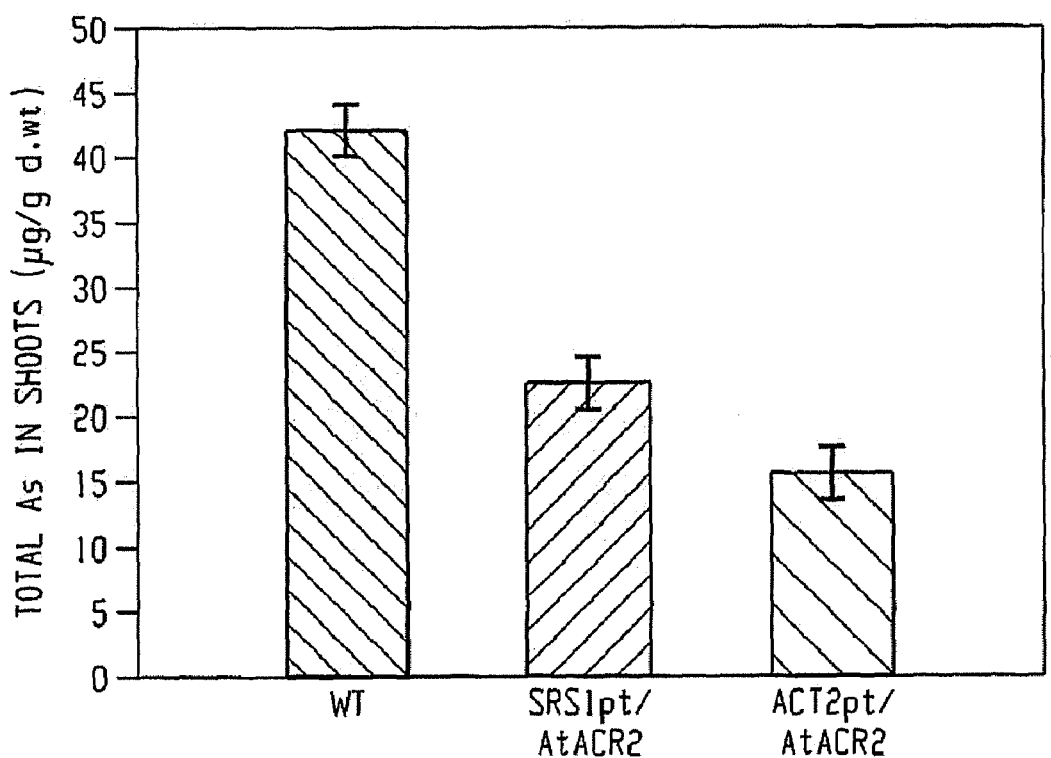
FIG. 7 shows arsenic accumulation in the AtACR2 *Arabidopsis* lines.
Figure 8:
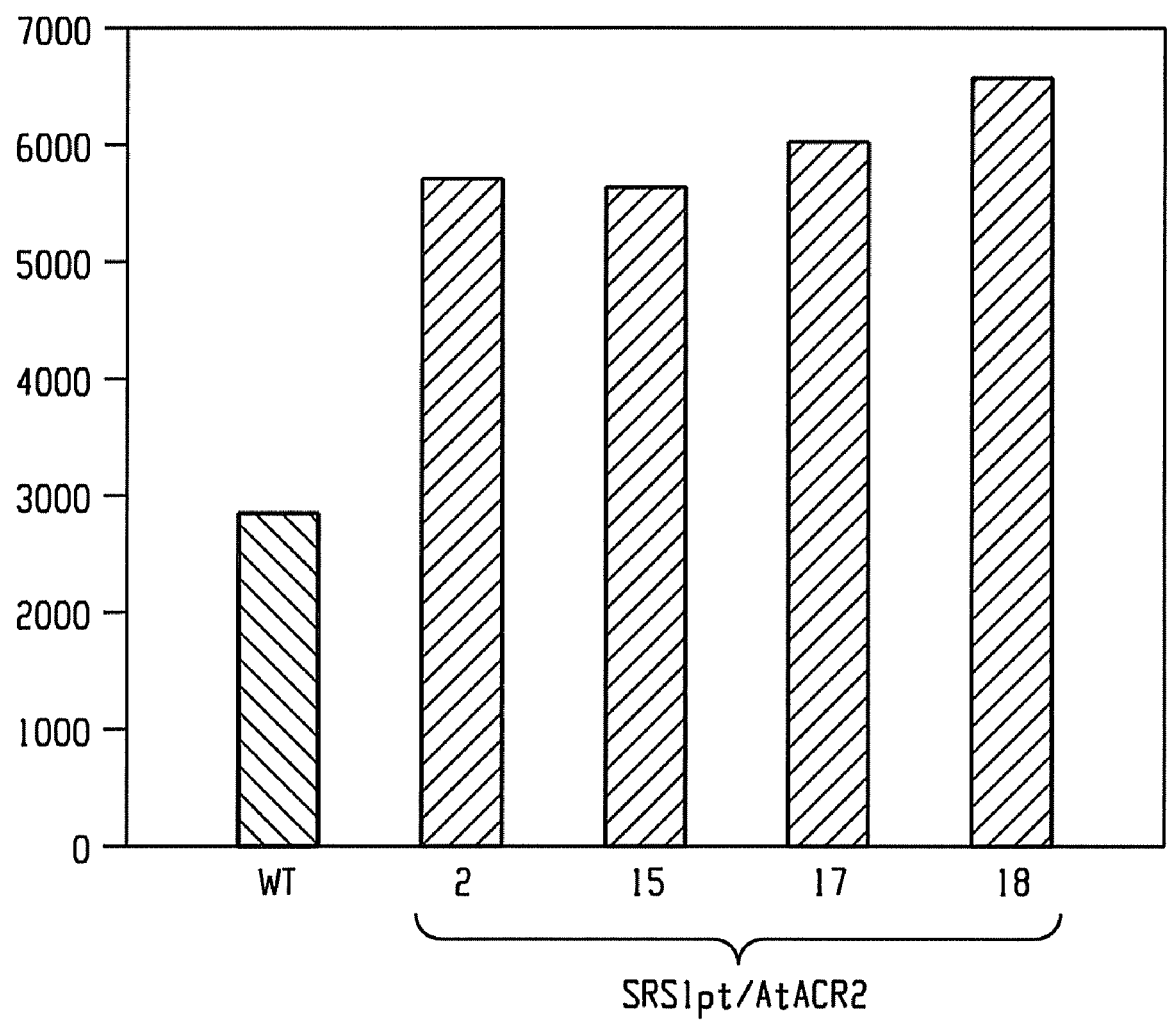
FIG. 8 shows the phosphorous uptake in transgenic *Arabidopsis* lines that overexpress AtACR2.

*Arabidopsis* AtACR2 was expressed under the control of a constitutive promoter (ACT2pt::AtACR2) and a leaf-specific promoter (SRS1pt::ACR2) in transgenic *Arabidopsis* plants. We selected several kanamycin resistant transgenic lines and used anti-AtACR2 monoclonal antibodies raised in our lab to quantify the expression levels of AtACR2 protein. Western analysis of the selected lines showed a 12- to 20-fold increase in expression level of AtACR2 protein in shoot tissue. When grown on 150-200 mM arsenate, all of these lines showed significantly high level of AsV resistance and accumulated 6- to 7-fold more biomass. FIG. 6. Further, when grown on media containing 75 mM AsV, AtACR2 overexpressing transgenic lines accumulated 2- to 3-fold less As in aboveground tissues as compared to wild-type controls. FIG. 7. For As extraction, transgenic and wild type plants were grown at lower concentration (75 mM) in order to avoid the growth inhibition in wild-type plants. As arsenate competes with phosphate for uptake in plants via high affinity phosphate transporters, we analyzed the total phosphate concentration in the transgenic and control plants. The reduced uptake of arsenic in these plants leads to increased phosphate uptake in the aboveground tissues thus enhancing plant productivity. FIG. 8. Total phosphorous in microgram P/gram dry weight was measured in several transgenic lines when grown on 1/2× MS media supplemented with 150 mM arsenate and grown for three weeks. As shown in FIG. 8, the SRS1pt::AtACR2 transgenic plants accumulated 2-fold more total phosphorous than wild type plants.

Figure 9:
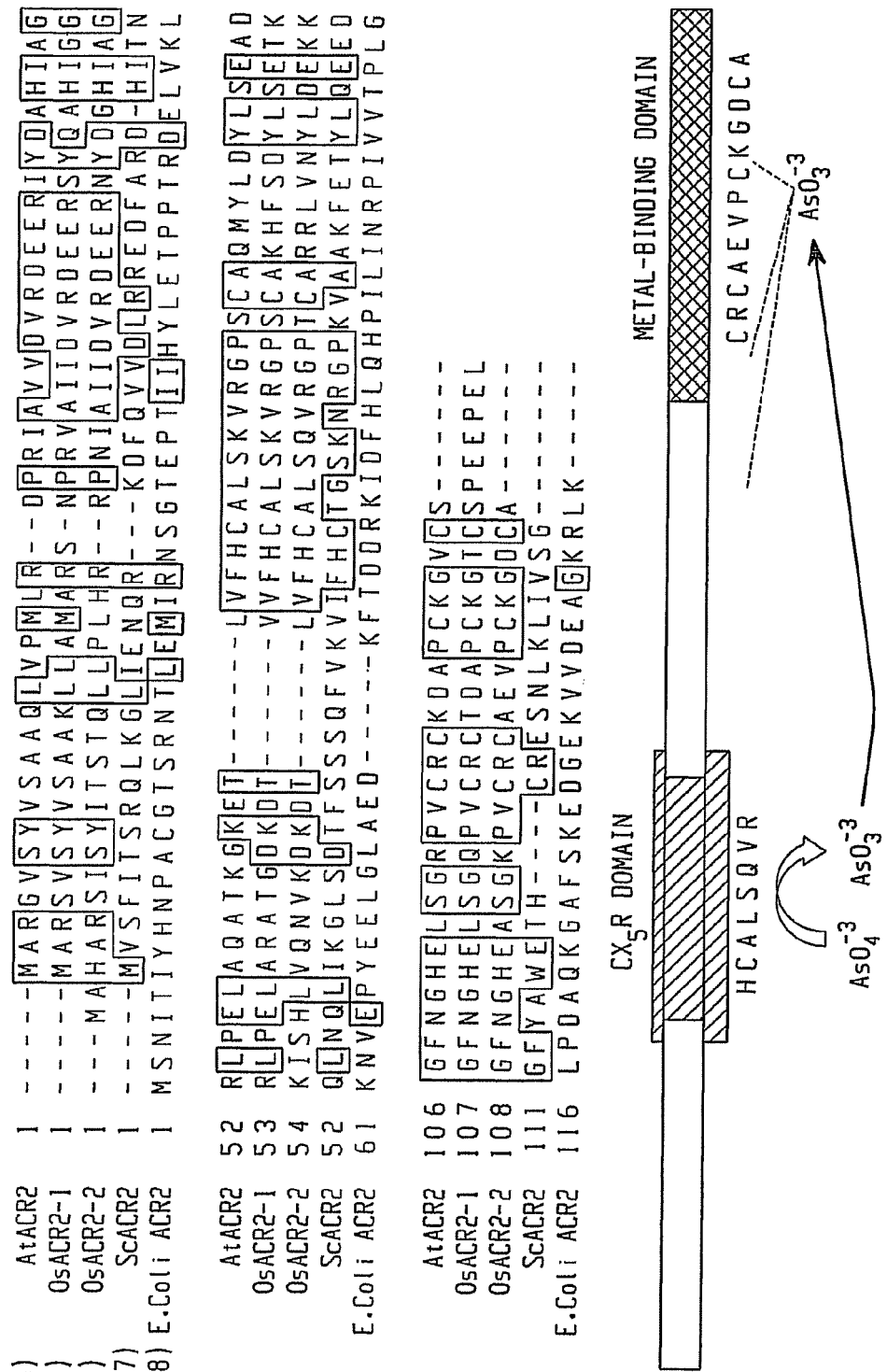
FIG. 9 shows the sequence alignment and predicted structures of plant, yeast, and bacterial arsenate reductases: (SEQ ID NO:5) AtACR2, (SEQ ID NO:6) OsACR2-1, (SEQ ID NO:7) OsACR2-2, (SEQ ID NO:27) ScACR2, and (SEQ ID NO:28) *E. coli* ACR2.

These results were unexpected because prior research had demonstrated that the overexpression of bacterial ArsC protein caused arsenic sensitivity in plants whereas overexpression of *Arabidopsis* AtACR2 provided arsenic resistance in plants. Without being bound by theory, it is believed that the increase in arsenic resistance with the plant ACR2 protein is because of the presence of a highly cysteine-rich C-terminal domain that is missing from the bacterial ArsC protein. As shown in FIG. 9, the plant arsenate reductases contain a cysteine-rich metal-binding C-terminal domain (double arrow line), whereas, the bacterial ArsC and yeast ScACR2 lack this domain. The replacement of cysteine residues with serine in the C-terminal domain of AtACR2 abolished the arsenic resistance in plants. Therefore, we suggest that AtACR2 enzymatically reduces arsenate to arsenite by the catalytic domain 'HCX$_5$R' and the generated arsenite binds to the cysteine-rich metal-binding C-terminal domain and hence provides arsenic tolerance. Overexpression of the catalytic domain, without the cysteine-rich metal-binding C-terminal domain, as with the bacterial ArsC protein, may result in an increase in free arsenite within the plant thereby causing arsenic sensitivity.

Figure 10:
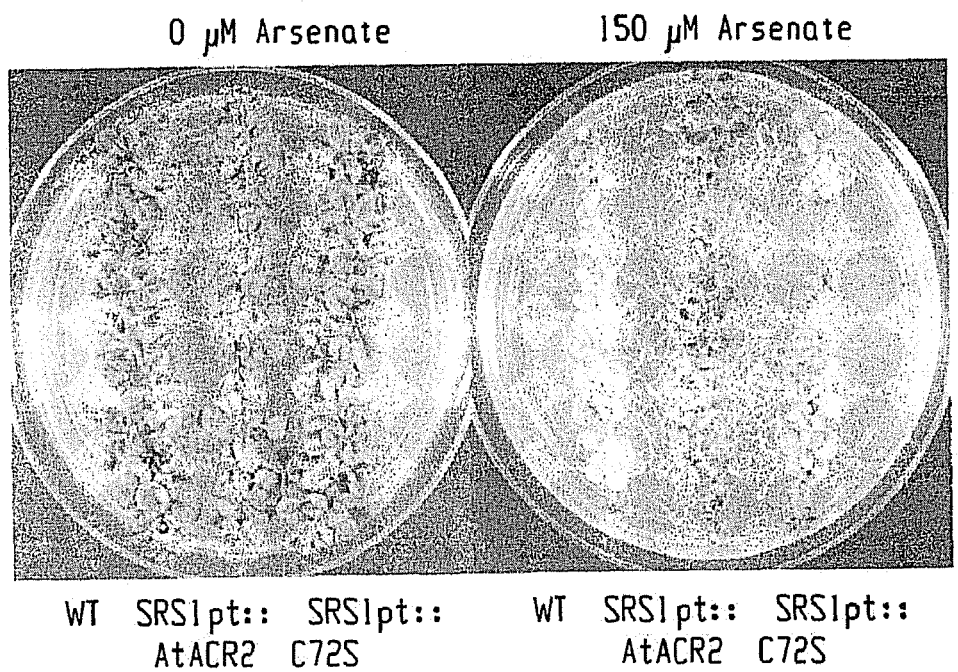
FIG. 10 shows the arsenic resistance in transgenic *Arabidopsis* lines that overexpress mutant forms of AtACR2.

The exact mechanism of the resistance and decreased arsenic uptake in shoot tissue of AtACR2 overexpression lines is not known yet. This is presumably due to the efficient reduction of AsV to AsIII in shoot tissues and further binding of AsIII to the C-terminal metal-binding domain. As we have mentioned previously, AtACR2 gene sequences have a catalytic arsenate reductase domain, $HCX_5R$, in the middle and a cysteine-rich C-terminal putative metal-binding domain. We propose that this gene has a dual function, both AsV reduction as well as AsIII-binding. The AsV is reduced to AsIII by "$HCX_5R$" domain and then AsIII is further bound to cysteine-rich C-terminal metal-binding domain. This mechanism of turnover of AsV reduction and subsequent binding of AsIII may be controlled by a negative feedback mechanism and thus causes less translocation of As from root to shoot tissues. In order to further elucidate the mechanism of As tolerance and reduction in As uptake and the role of conserved cysteine residues in "$HCX_5R$" and C-terminal metal-binding domain, we replaced cysteine residue at position 72 with serine in the catalytic domain (C72S) and three cysteine residues at position 120, 122, and 127 with serine in the cysteine-rich C-terminal domain (C120S, C122S, C122S). The mutant form of AtACR2 was overexpressed under SRS1pt vector in *Arabidopsis* and plants were analyzed on media containing arsenate. The initial results showed that plants overexpressing mutant $AtACR2_{C72S}$, lost AsV resistance and grew similar to wild-type plants. FIG. 10. Plants overexpressing double mutant ($AtAC2_{C122S, C127S}$) and triple mutant ($AtACR2_{C120S, C122S, C127S}$), also lost the arsenate resistance.

Figure 11:
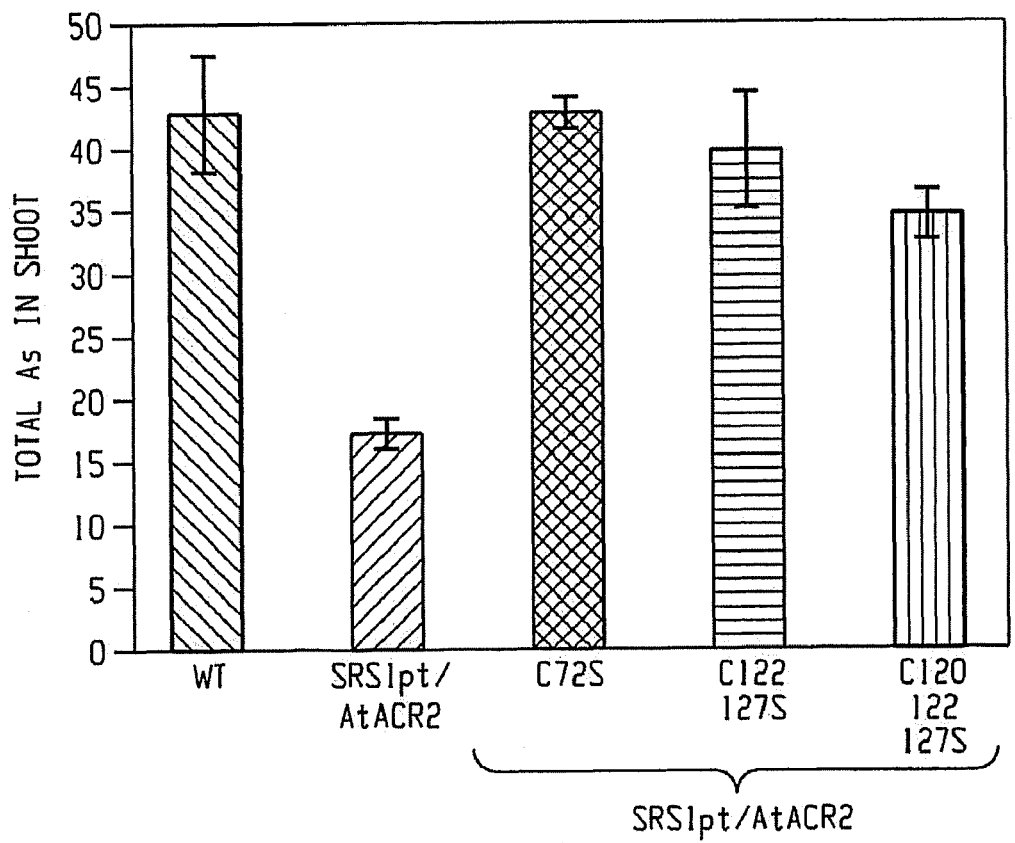
FIG. 11 shows the arsenic accumulation in transgenic *Arabidopsis* lines that overexpress mutant forms of AtACR2.

Additionally, the total arsenic uptake showed that these plants overexpressing the mutated proteins accumulated arsenic similar to wild-type controls, whereas, SRS1pt::AtACR2 overexpressing plants accumulated 2- to 3-fold less arsenic. FIG. 11. These experiments suggest that the cysteine residue in conserved catalytic domain "$HCX_5R$" is required for reduction of AsV to AsIII by AtACR2 and the cysteine residues in the C-terminal metal-binding domain are required for AsIII-binding to provide AsV resistance as shown in the predicted model in FIG. 9.

Figure 12:
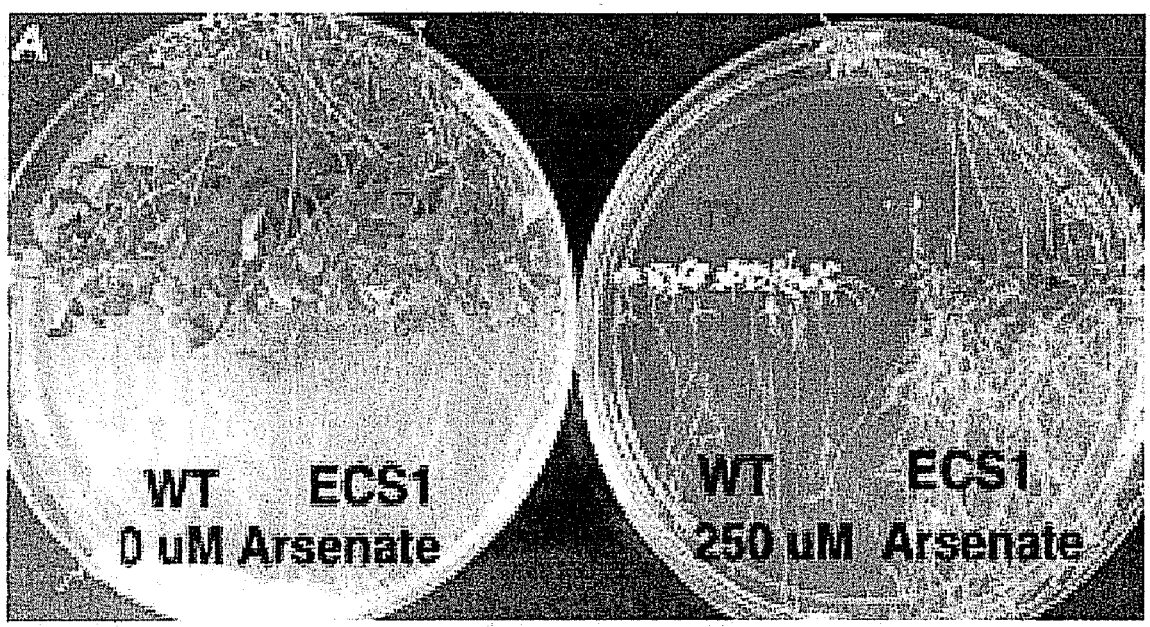
FIG. 12 shows transgenic *Arabidopsis* lines that overexpress gamma-ECS.

The gamma-ECS phytochelatin biosynthetic gene under the control of a constitutive promoter (ACT2pt::gamma-ECS) was further expressed. The transgenic plants were highly resistant to 250 micromolar arsenate that was toxic to wild type control *Arabidopsis*. FIG. 12.

Example 9

Analysis of Transgenic Rice Lines

Overexpression of *Arabidopsis* AtACR2 in rice: *Arabidopsis* AtACR2 and rice OsACR2 genes were placed under the control of the rice ACT1 promoter in a pCambia binary vector for rice (*Oryza sativa* variety *japonica* cultivar Nipponbare) transformation as shown in gene constructs in FIG. 3. Rice plants transformed with the ACT1/AtACR2/nos gene construct were tested for arsenate resistance. The scutellum derived rice calli were infected with *Agrobacterium* strain LBA4404 containing pCAMBIA1300 with the ACT1/AtACR2/nos cassette and transgenic rice plants were raised as described in Example 5.

RT-PCR analysis of Rice OsACR2genes: From the amplification of OsACR2-1 and OsACR2-2 cDNAs by RT-PCR from rice seedlings mRNA, it is clear that both cDNAs are constitutively expressed both in shoot and root tissues. FIG. 1. However, it is not known if AtACR2 is regulated by arsenate, arsenite, phosphate, or other heavy metal stresses. Therefore, we investigated the regulation of OsACR2 genes by isolating the mRNA from plant tissues exposed to 150 micromolar AsV and 40 micromolar AsIII. We isolated total RNA from these tissues using the Qiagen RNAeasy Plant RNA extraction kit. We synthesized 1st strand cDNA from total RNA by RT-PCR using Invitrogen RT-PCR kit (Invitrogen, Inc.) and performed a semi-quantitative RTR-PCR in order to study if OsACR2-1 and OsACR2-2 transcripts are up-regulated by AsV and AsIII. The PCR was performed using the gene-specific primers (SEQ ID Nos. 17-20) with PCR conditions: 1 cycle of 94° C. for 2 minute, 35 cycles of 94° C. for 45 seconds, 52° C. for 45 seconds and 72° C. for I minute and 1 cycle of 72° C. for 10 minutes. The PCR products were resolved on 1% agarose gel. As shown in FIG. 2, both genes were up regulated in response to AsV, whereas, only OsACR2;1 is upregulated in the AsIII exposed plants. We propose that altering the expression of these plant arsenate reductases and other arsenic-binding proteins could play a vital role in enhancing resistance and decreased uptake of arsenic in shoots and seeds in rice and thus subsequently prevents the entry of arsenic into the food chain.

Figure 13:
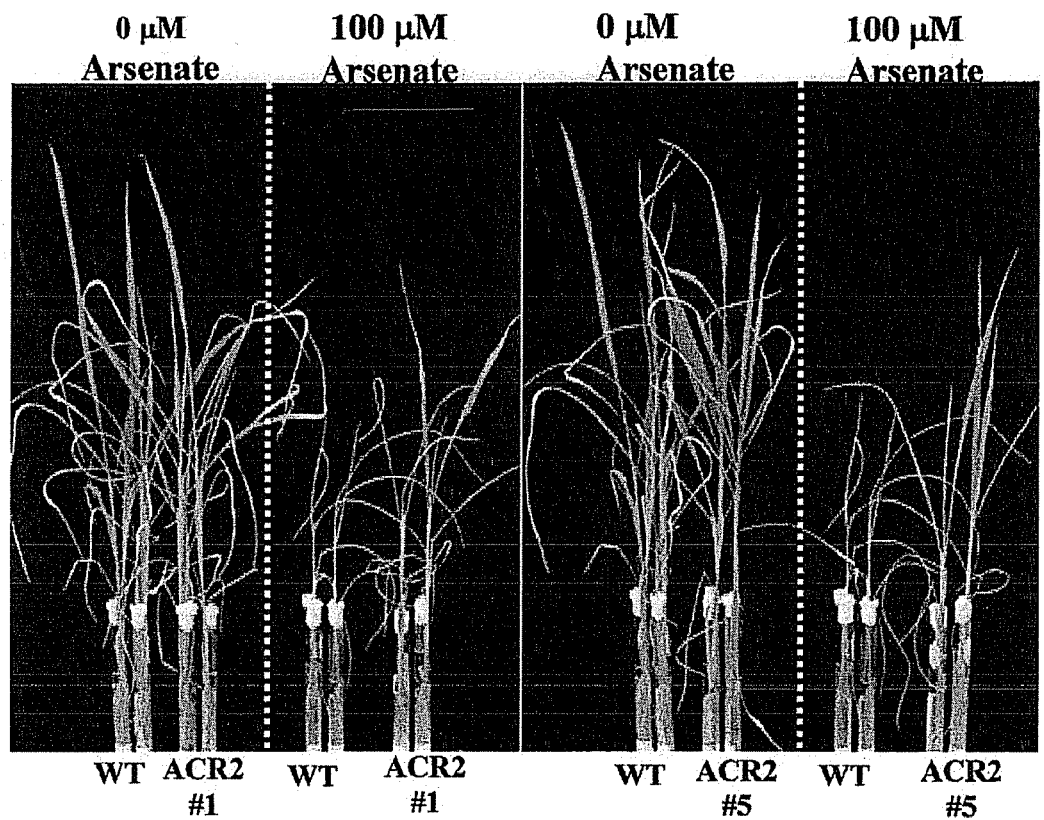
FIG. 13 shows the increased arsenic resistance and biomass in transgenic rice lines that overexpress AtACR2.

Arsenic resistance of transgenic rice plants: Seven hygromycin resistant transgenic rice lines were selected and transferred to soil in a greenhouse to raise the T1 generation of seeds. The transgenic rice seeds were surface sterilized and grown on rice tissue culture media. Two-week old hygromycin-resistant rice transgenic plants and control wild type plants were transferred to hydroponic media containing 1/x MS media and were acclimatized in the hydroponic system for one week. The transgenic plants were then transferred to fresh hydroponic media supplemented with 100 mM arsenate. These plants were continuously grown for next 35 days on the arsenate-containing media with frequent replacement of the media with fresh hydroponic media containing 100 mM arsenate. These plants were analyzed for arsenate resistance and uptake. All seven transgenic rice lines when grown in hydroponic media containing 100 mM arsenate showed strong resistance to arsenate as compared to wild type controls and all accumulated 6-7 fold more biomass compared to wild type controls. Two representative transgenic rice lines (ACR2 #1 and ACR #5) are shown in FIG. 13. The wild type control plants at 100 mM arsenate died after 35 days whereas transgenic plants stayed healthy and green.

Figure 14:
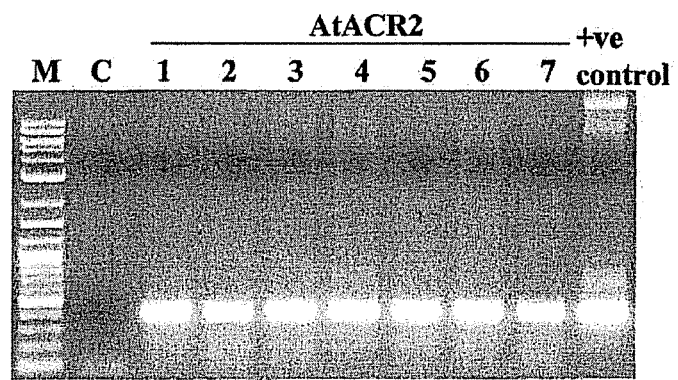
FIG. 14 shows the expression of AtACR2 cDNA in transgenic rice.

Confirmation of the expression of AtACR2 in transgenic rice: The expression of *Arabidopsis* AtACR2 in transgenic rice lines was analyzed by RT-PCR. The total RNA isolated from the transgenic rice and control plant seedlings using Qiagen RNAeasy Plant RNA extraction kit was used to synthesize $1^{st}$ strand cDNA using Invitrogen RT-PCR kit (Invitrogen, Inc.) and performed a semi-quantitative RTR-PCR. AtACR2 specific primers were used. (SEQ ID Nos. 15, 16). The RT-PCR conditions were same as described above in the "RT-PCR analysis of OsACR2 genes" section. The RT-PCR results showed the presence of an approximately 400 bp corresponding to the AtACR2 cDNA size in all seven transgenic rice lines whereas no expression was detected in the control wild type plants as shown in FIG. 14. Plasmid DNA from bacterial cells overexpressing AtACR2 gene was used as positive control.

A transgenic plant comprising a recombinant plant arsenate reductase coding sequence operatively linked to a plant-expressible transcription regulatory sequence will advantageously provide improved arsenic resistance in plants such as crop plants and other economically important plants. The arsenic-resistant transgenic plant will further provide improved phosphate uptake thereby enhancing plant productivity. In addition, the amount of arsenic introduced into the food chain can be reduced by separately harvesting the plant tissues from the arsenic-resistant transgenic plant that contain low amounts of arsenic.

The terms "first," "second," and the like, "primary," "secondary," and the like, as used herein do not denote any order, quantity, or importance, but rather are used to distinguish one element from another. The terms "a" and "an" do not denote a limitation of quantity, but rather denote the presence of at least one of the referenced item.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A transgenic plant transformed with a recombinant polynucleotide comprising an isolated plant arsenate reductase coding sequence operatively linked to a plant-expressible transcription regulatory sequence;
   wherein the plant arsenate reductase coding sequence is greater than or equal to about 95% homologous with a sequence selected from the group consisting of SEQ ID NO:1, SEQ ID NO:2, SEQ ID NO:3, SEQ ID NO:4, and SEQ ID NO:21, wherein the plant arsenate reductase coding sequence encodes a polypeptide having arsenate reductase activity; and
   wherein the transgenic plant is resistant to a metal or metal ion.

2. The transgenic plant of claim 1, wherein the transgenic plant is selected from the group consisting of *Arabidopsis thaliana*, canola, sunflower, tobacco, mustard, crambe, sugar beet, cotton, maize, wheat, barley, rice, sorghum, mangelwurzels, tomato, mango, peach, apple, pear, strawberry, banana, melon, potato, carrot, lettuce, cabbage, onion, soybean, sugar cane, pea, field beans, poplar, grape, citrus, alfalfa, rye, oats, turf and forage grasses, flax and oilseed rape, nut producing plants, *Brachypodium distachyon*, and switchgrass.

3. The transgenic plant of claim 1, wherein the transgenic plant is rice.

4. The transgenic plant of claim 1, wherein the transgenic plant is *Arabidopsis thaliana*.

5. The transgenic plant of claim 1, wherein the plant arsenate reductase coding sequence is derived from *Arabidopsis thaliana, Brassica, Crambe*, or rice.

6. The transgenic plant of claim 1, wherein the plant arsenate reductase coding sequence is selected from the group consisting of SEQ ID NO:1, SEQ ID NO:2, SEQ ID NO:3, SEQ ID NO:4, and SEQ ID NO:21.

7. The transgenic plant of claim 1, wherein the plant arsenate reductase coding sequence is SEQ ID NO:1.

8. The transgenic plant of claim 1, wherein the plant-expressible transcription regulatory sequence comprises a constitutive promoter, an inducible promoter, a tissue-specific promoter, an organ-specific promoter, or a combination of one of the foregoing promoters.

9. The transgenic plant of claim 7, wherein the constitutive promoter is derived from a cauliflower mosaic virus 35S promoter, a cauliflower mosaic virus 19S promoter, an *Agrobacterium tumefaciens* T-DNA nos promoter, an *Agrobacterium tumefaciens* T-DNA ocs promoter, an *Agrobacterium tumefaciens* T-DNA mas promoter, a plant ACT2 promoter, a plant ACT1 promoter, a plant ubiquitin promoter, or a combination comprising at least one of the foregoing promoters.

10. The transgenic plant of claim 9, wherein the metal or metal ion is arsenic, arsenate, arsenite, or a combination comprising one of the foregoing metals or metal ions.

11. The transgenic plant of claim 1, wherein greater than or equal to about 25% of transgenic plants are resistant to a concentration of metal or metal ion that is lethal to wild type plants.

12. The transgenic plant of claim 1, wherein the transgenic plant accumulates less than or equal to about 75% of the total metal or metal ion accumulated in a wild type plant.

13. The transgenic plant of claim 1, wherein the transgenic plant accumulates greater than or equal to about 25% of the total phosphate accumulated in a wild type plant.

14. The transgenic plant of claim 1, wherein the transgenic plant accumulates greater than or equal to about two-fold more total biomass than the total biomass accumulated in a wild type plant.

15. The transgenic plant of claim 1 further comprising a recombinant polynucleotide comprising a phytochelatin biosynthetic enzyme coding sequence.

16. The transgenic plant of claim 15, wherein the phytochelatin biosynthetic enzyme coding sequence encodes a gamma-glutamyl-cysteine synthase, a glutathione synthase, or a phytochelatin synthase.

17. The transgenic plant of claim 15, wherein the phytochelatin biosynthetic enzyme coding sequence is greater than or equal to about 95% homologous with a sequence selected from the group consisting of SEQ ID NO:9, SEQ ID NO:10, and SEQ ID NO:11, wherein the phytochelatin biosynthetic enzyme coding sequence has phytochelatin biosynthesis activity.

18. The transgenic plant of claim 15, wherein the phytochelatin biosynthetic enzyme coding sequence is selected from the group consisting of SEQ ID NO:9, SEQ ID NO:10, and SEQ ID NO:11.

19. A method to limit metal or metal ion accumulation in a harvested plant tissue comprising
   growing a transgenic plant comprising a recombinant polynucleotide comprising a plant arsenate reductase coding sequence operatively linked to a plant-expressible transcription regulatory sequence;
   wherein the plant arsenate reductase coding sequence is greater than or equal to about 95% homologous with a sequence selected from the group consisting of SEQ ID NO:1, SEQ ID NO:2, SEQ ID NO:3, SEQ ID NO:4, and SEQ ID NO:21, wherein the plant arsenate reductase coding sequence encodes a polypeptide having arsenate reductase activity; and
   harvesting plant tissue having reduced metal or metal ion accumulation.

20. The method of claim 19, wherein the transgenic plant is selected from the group consisting of *Arabidopsis thaliana*, canola, sunflower, tobacco, mustard, crambe, sugar beet, cotton, maize, wheat, barley, rice, sorghum, mangel-wurzels, tomato, mango, peach, apple, pear, strawberry, banana, melon, potato, carrot, lettuce, cabbage, onion, soybean, sugar cane, pea, field beans, poplar, grape, citrus, alfalfa, rye, oats, turf and forage grasses, flax and oilseed rape, nut producing plants, *Brachypodium distachyon*, and switchgrass.

21. The method of claim 19, wherein the transgenic plant is rice.

22. The method of claim 19, wherein the transgenic plant is *Arabidopsis thaliana*.

23. The method of claim 19, wherein the harvesting plant tissue comprises separating plant tissue having reduced metal or metal ion accumulation from plant tissue having increased metal or metal ion accumulation.

24. The method of claim 19, wherein the plant tissue having reduced metal or metal ion accumulation has greater than or equal to about 25% of the total metal or metal ion as the plant tissue having increased metal or metal ion accumulation.

25. The method of claim 19, wherein the metal or metal ion is arsenic, arsenate, arsenite, or a combination comprising one of the foregoing metals or metal ions.

26. The method of claim 19, wherein the plant arsenate reductase coding sequence is derived from *Arabidopsis thaliana*, *Brassica*, *Crambe*, or rice.

27. The method of claim 19, wherein the plant arsenate reductase coding sequence is selected from the group consisting of SEQ ID NO:1, SEQ ID NO:2, SEQ ID NO:3, SEQ ID NO:4, and SEQ ID NO:21.

28. The method of claim 19, wherein the plant arsenate reductase coding sequence is SEQ ID NO:1.

29. The method of claim 19, wherein the plant-expressible transcription regulatory sequence comprises a constitutive promoter, an inducible promoter, a tissue-specific promoter, an organ-specific promoter, or a combination of one of the foregoing promoters.

30. The method of claim 19, wherein the transgenic plant further comprises a recombinant polynucleotide comprising a phytochelatin biosynthetic enzyme coding sequence.

31. A method for producing a metal or metal ion resistant plant comprising
   introducing a recombinant polynucleotide comprising an plant arsenate reductase coding sequence operatively linked to a plant-expressible transcription regulatory sequence into a plant cell or plant tissue;
   producing a transgenic plant cell or tissue comprising the recombinant polynucleotide;
   wherein the plant arsenate reductase coding sequence is greater than or equal to about 95% homologous with a sequence selected from the group consisting of SEQ ID NO:1, SEQ ID NO:2, SEQ ID NO:3, SEQ ID NO:4, and SEQ ID NO:21, wherein the plant arsenate reductase coding sequence encodes a polypeptide having arsenate reductase activity; and
   regenerating the transgenic plant cell or transgenic plant tissue to provide a metal or metal ion resistant plant.

32. The method of claim 31, wherein the transgenic plant is selected from the group consisting of *Arabidopsis thaliana*, canola, sunflower, tobacco, mustard, crambe, sugar beet, cotton, maize, wheat, barley, rice, sorghum, mangel-wurzels, tomato, mango, peach, apple, pear, strawberry, banana, melon, potato, carrot, lettuce, cabbage, onion, soybean, sugar cane, pea, field beans, poplar, grape, citrus, alfalfa, rye, oats, turf and forage grasses, flax and oilseed rape, nut producing plants, *Brachypodium distachyon*, and switchgrass.

33. The method of claim 31, wherein the transgenic plant is rice.

34. The method of claim 31, wherein the transgenic plant is *Arabidopsis thaliana*.

35. The method of claim 31, wherein the plant arsenate reductase coding sequence is derived from *Arabidopsis thaliana*, *Brassica*, *Crambe*, or rice.

36. The method of claim 31, wherein the plant arsenate reductase coding sequence is selected from the group consisting of SEQ ID NO:1, SEQ ID NO:2, SEQ ID NO:3, SEQ ID NO:4, and SEQ ID NO:21.

37. The method of claim 31, wherein the plant arsenate reductase coding sequence is SEQ ID NO:1.

38. The method of claim 31, wherein the plant-expressible transcription regulatory sequence comprises a constitutive promoter, an inducible promoter, a tissue-specific promoter, an organ-specific promoter, or a combination comprising one of the foregoing promoters.

39. The method of claim 31, wherein the transgenic plant further comprises a recombinant polynucleotide comprising a phytochelatin biosynthetic enzyme coding sequence.

40. The method of claim 31, wherein the transgenic plant is resistant to arsenic, arsenate, arsenite, or a combination comprising one of the foregoing metals or metal ions.

41. The method of claim 31, wherein greater than or equal to about 25% of the transgenic plants are resistant to a concentration of metal or metal ion that is lethal to wild type plants.

42. The method of claim 31, wherein the transgenic plants accumulate less than or equal to about 75% of the total metal or metal ion accumulated in wild type plants.

43. The method of claim 31, wherein the transgenic plants accumulate greater than or equal to about 25% of the total phosphate accumulated in wild type plants.

44. The method of claim 31, wherein the transgenic plants accumulate greater than or equal to about two-fold more total biomass than the total biomass accumulated in wild type plants.

* * * * *

SEQUENCE LISTING

<160> NUMBER OF SEQ ID NOS: 28

<210> SEQ ID NO 1
<211> LENGTH: 399
<212> TYPE: DNA
<213> ORGANISM: Arabidopsis thaliana

<400> SEQUENCE: 1

```
atggcgatgg cgagaagcat ctcttacatc acctctactc agcttctccc tcttcatcgt      60
cgtcccaaca tcgccatcat cgatgtcagg gatgaagaga ggaattatga cgggcatata     120
gctggatcgc tacactatgc gagtggctcg tttgatgaca agatctcaca tcttgttcaa     180
aatgtcaagg acaaagacac acttgtcttc cattgtgcct tgagccaggt tcgtggccct     240
acttgtgcga gaaggctcgt gaattatctt gatgagaaga agaagatac tggaatcaaa      300 aacatcatga tcttggaacg cggctttaac ggttgggaag cttctggaaa accggtctgc     360
cgctgtgcag aggttccttg caagggcgat tgcgcctaa                             399
```

<210> SEQ ID NO 2
<211> LENGTH: 414
<212> TYPE: DNA
<213> ORGANISM: Oryza sativa

<400> SEQUENCE: 2

```
atggcgcgga gcgtgtcgta cgtgtcggcg gcgaagctcc tggccatggc gcgcagcaac      60
ccccgcgtcg ccatcatcga cgtcagggac gaggagagga gctaccaggc gcacatcggg     120
gggtcgcacc acttctccag ccgcagcttc gcggcgcggc tgccggagct cgcgcgtgcc     180
accggcgaca aggacaccgt cgtcttccac tgcgccctca gcaaggtgcg aggtccatcg     240
tgtgccaaga tgttctccga ctatctatct gagaccaagg aagaatcagg aacaaagaac     300
atcatggtgc tggaacgtgg gttcaatgga tgggagcttt cgggacaacc cgtttgccgg     360
tgcactgatg ccccttgcaa aggcacatgc tcacctgaag aacctgagtt gtaa            414
```

<210> SEQ ID NO 3
<211> LENGTH: 393
<212> TYPE: DNA
<213> ORGANISM: Oryza sativa

<400> SEQUENCE: 3

```
atggcgaggg gcgtctccta cgtttccgcg gcgcagctcg tccccatgct ccgggacccc      60
cggatcgccg tcgtcgatgt cagggacgaa gagaggatct acgacgcgca catcgccggc     120
tcgcatcatt acgccagcga cagcttcggg gagcggctgc cggagctggc ccaggccacc     180
aagggcaagg aaaccctcgt cttccactgt gccctcagca aggtgcgtgg cccatcttgt     240
gcgcaaatgt atctggacta tttgtcagag gctgatgaag attcagatgt aaagaacatc     300
atggtccttg aacgtggatt taatggatgg gaactttcag ggaggcctgt ttgccgctgc     360
```
aaggacgctc cttgcaaggg tgtgtgctct tga  393

```
<210> SEQ ID NO 4
<211> LENGTH: 396
<212> TYPE: DNA
<213> ORGANISM: Brassica napus

<400> SEQUENCE: 4
```
atggcggcga agcatctc ttacatcacc tcaactcagc tccttcctct tcatcgtcgt  60
cccaacatag ccatcatcga tgtcagggat gaagagaggg actatgatgg catatagct  120 ggctcgctac actatgctag tggctctttt gaagacagga tctctcatct tgttcaaaat  180
gtcaaggata agacacact tgttttccat tgtgctttga ccaggttcg tggcccaaca  240 tgtgctagaa gactggtgaa ttacctcgac gagaagaaac aagaaactgg aataaaaaac  300
ataatgatct ggaacgtgg cttcaatggc tgggaagctg ctggtaaacc ggtttgccgc  360
tgcgccgacg ttccttgcaa gggcgactgc acctaa  396

```
<210> SEQ ID NO 5
<211> LENGTH: 132
<212> TYPE: PRT
<213> ORGANISM: Arabidopsis thaliana

<400> SEQUENCE: 5
```

Met Ala Met Ala Arg Ser Ile Ser Tyr Ile Thr Ser Thr Gln Leu Leu
1               5                   10                  15

Pro Leu His Arg Arg Pro Asn Ile Ala Ile Ile Asp Val Arg Asp Glu
                20                  25                  30

Glu Arg Asn Tyr Asp Gly His Ile Ala Gly Ser Leu His Tyr Ala Ser
            35                  40                  45

Gly Ser Phe Asp Asp Lys Ile Ser His Leu Val Gln Asn Val Lys Asp
        50                  55                  60

Lys Asp Thr Leu Val Phe His Cys Ala Leu Ser Gln Val Arg Gly Pro
65                  70                  75                  80

Thr Cys Ala Arg Arg Leu Val Asn Tyr Leu Asp Glu Lys Lys Glu Asp
                85                  90                  95

Thr Gly Ile Lys Asn Ile Met Ile Leu Glu Arg Gly Phe Asn Gly Trp
            100                 105                 110

Glu Ala Ser Gly Lys Pro Val Cys Arg Cys Ala Glu Val Pro Cys Lys
        115                 120                 125

Gly Asp Cys Ala
    130

```
<210> SEQ ID NO 6
<211> LENGTH: 137
<212> TYPE: PRT
<213> ORGANISM: Oryza sativa

<400> SEQUENCE: 6
```

Met Ala Arg Ser Val Ser Tyr Val Ser Ala Ala Lys Leu Leu Ala Met
1               5                   10                  15

Ala Arg Ser Asn Pro Arg Val Ala Ile Ile Asp Val Arg Asp Glu Glu
                20                  25                  30

Arg Ser Tyr Gln Ala His Ile Gly Gly Ser His His Phe Ser Ser Arg
            35                  40                  45

Ser Phe Ala Ala Arg Leu Pro Glu Leu Ala Arg Ala Thr Gly Asp Lys
        50                  55                  60

```
Asp Thr Val Val Phe His Cys Ala Leu Ser Lys Val Arg Gly Pro Ser
65                  70                  75                  80

Cys Ala Lys Met Phe Ser Asp Tyr Leu Ser Glu Thr Lys Glu Glu Ser
                85                  90                  95

Gly Thr Lys Asn Ile Met Val Leu Glu Arg Gly Phe Asn Gly Trp Glu
            100                 105                 110

Leu Ser Gly Gln Pro Val Cys Arg Cys Thr Asp Ala Pro Cys Lys Gly
        115                 120                 125

Thr Cys Ser Pro Glu Glu Pro Glu Leu
    130                 135

<210> SEQ ID NO 7
<211> LENGTH: 130
<212> TYPE: PRT
<213> ORGANISM: Oryza sativa

<400> SEQUENCE: 7

Met Ala Arg Gly Val Ser Tyr Val Ser Ala Ala Gln Leu Val Pro Met
1               5                   10                  15

Leu Arg Asp Pro Arg Ile Ala Val Val Asp Val Arg Asp Glu Glu Arg
                20                  25                  30

Ile Tyr Asp Ala His Ile Ala Gly Ser His His Tyr Ala Ser Asp Ser
            35                  40                  45

Phe Gly Glu Arg Leu Pro Glu Leu Ala Gln Ala Thr Lys Gly Lys Glu
        50                  55                  60

Thr Leu Val Phe His Cys Ala Leu Ser Lys Val Arg Gly Pro Ser Cys
65                  70                  75                  80

Ala Gln Met Tyr Leu Asp Tyr Leu Ser Glu Ala Asp Glu Asp Ser Asp
                85                  90                  95

Val Lys Asn Ile Met Val Leu Glu Arg Gly Phe Asn Gly Trp Glu Leu
            100                 105                 110

Ser Gly Arg Pro Val Cys Arg Cys Lys Asp Ala Pro Cys Lys Gly Val
        115                 120                 125

Cys Ser
    130

<210> SEQ ID NO 8
<211> LENGTH: 131
<212> TYPE: PRT
<213> ORGANISM: Brassica napus

<400> SEQUENCE: 8

Met Ala Ala Arg Ser Ile Ser Tyr Ile Thr Ser Thr Gln Leu Leu Pro
1               5                   10                  15

Leu His Arg Arg Pro Asn Ile Ala Ile Ile Asp Val Arg Asp Glu Glu
                20                  25                  30

Arg Asn Tyr Asp Gly His Ile Ala Gly Ser Leu His Tyr Ala Ser Gly
            35                  40                  45

Ser Phe Glu Asp Arg Ile Ser His Leu Val Gln Asn Val Lys Asp Lys
        50                  55                  60

Asp Thr Leu Val Phe His Cys Ala Leu Ser Gln Val Arg Gly Pro Thr
65                  70                  75                  80

Cys Ala Arg Arg Leu Val Asn Tyr Leu Asp Glu Lys Lys Gln Glu Thr
                85                  90                  95

Gly Ile Lys Asn Ile Met Ile Leu Glu Arg Gly Phe Asn Gly Trp Glu
            100                 105                 110
```

Ala Ala Gly Lys Pro Val Cys Arg Cys Ala Asp Val Pro Cys Lys Gly
        115                 120                 125

Asp Cys Thr
    130

<210> SEQ ID NO 9
<211> LENGTH: 2098
<212> TYPE: DNA
<213> ORGANISM: Escherichia coli

<400> SEQUENCE: 9
gttaactaac gttatccttg ggcgtttctt tccattgcgt aaaacatcgc gctggcaaga      60
gaaagctacc ggctggctga acgctatggt gcagtcacg ctattattaa gctggatgcc     120
cgtggttggc gatttactgt gtctgttagc gggatggatg cgcatctcgt ggggaccggt     180
aatcttttt ttgtgccttg gtaaagcgtt acgctatgtt gcagttgcag cagcgaccgt     240
tcagggcatg atgtggtggc actaattgta ggcctgcaca tatggtcacc attacagtta     300
tgctaattaa aacgattttg acaggcggga ggtcaatttg atcccggacg tatcacaggc     360
gctggcctgg ctggaaaaac atcctcaggc gttaaagggg atacagcgtg ggctggagcg     420
cgaaactttg cgtgttaatg ctgatggcac actggcaaca acaggtcatc ctgaagcatt     480
aggttccgca ctgacgcaca atggattac taccgatttt gcggaagcat tgctggaatt     540
cattacacca gtggatggtg atattgaaca tatgctgacc tttatgcgcg atctgcatcg     600
ttatacggcg cgcaatatgg gcgatgagcg gatgttgccg ttaagtatgc catgctacat     660
cgcagaaggt caggacatcg aactggcaca gtacggcact tctaacaccg gacgctttaa     720
aacgctgtat cgtgaaggc tgaaaaatcg ctacggcgcg ctgatgcaaa ccatttccgg     780
cgtgcactac aatttctctt tgccaatggc attctggcaa gcgaagtgcg gtgatatctc     840
gggcgctgat gccaaagaga aaatttctgc gggctatttc cgcgttatcc gcaattacta     900
tcgtttcggt tgggtcattc cttatctgtt tggtgcatct ccggcgattt gttcttcttt     960
cctgcaagga aaaccaacgt cgctgccgtt tgagaaaacc gagtgcggta tgtattacct    1020
gccgtatgcg acctctcttc gtttgagcga tctcggctat accaataaat cgcaaagcaa    1080
tcttggtatt accttcaacg atcttttacga atacgtagcg ggccttaaac aggcaatcaa    1140
aacgccatcg gaagagtacg cgaagattgg tattgagaaa gacggtaaga ggctgcaaat    1200
caacagcaac gtgttgcaga ttgaaaacga actgtacgcg ccgattcgtc aaaacgcgt    1260
tacccgcagc ggcgagtcgc cttctgatgc gctgttacgt ggcggcattg aatatattga    1320
agtgcgttcg ctggacatca cccgttctc gccgattggt gtagatgaac agcaggtgcg    1380
attcctcgac ctgtttatgg tctggtgtgc gctggctgat gcaccggaaa tgagcagtag    1440
cgaacttgcc tgtacacgcg ttaactggaa ccgggtgatc ctcgaaggtc gcaaaccggg    1500
tctgacgctg ggtatcggct gcgaaaccgc acagttcccg ttaccgcagg tgggtaaaga    1560
tctgttccgc gatctgaaac gcgtcgcgca aacgctggat agtattaacg gcggcgaagc    1620
gtatcagaaa gtgtgtgatg aactggttgc ctgcttcgat aatcccgatc tgactttctc    1680
tgcccgtatc ttaaggtcta tgattgatac tggtattggc ggaacaggca agcatttgc    1740
agaagcctac cgtaatctgc tgcgtgaaga gccgctggaa attctgcgcg aagaggattt    1800
tgtagccgag cgcgagggct tcgaacgccg tcagcaggaa atggaagccg ctgataccga    1860
accgtttgcg gtgtggctgg aaaaacacgc ctgacagaaa agaaaaggc cactcgtgag    1920

-continued

| | |
|---|---|
| tggccaaaat tcatctctg aattcaggga tgatgataac aaatgcgcgt ctttcatata | 1980 |
| ctcagactcg cctgggaaga aagagttcag aaaattttta aaaaaattac cggaggtggc | 2040 |
| taaatgccgt tgttagatag cttcacagtc gatcatacc ggatggaagc gcctgcag | 2098 |

<210> SEQ ID NO 10
<211> LENGTH: 951
<212> TYPE: DNA
<213> ORGANISM: Escherichia coli

<400> SEQUENCE: 10

| | |
|---|---|
| atgatcaagc tcggcatcgt gatggacccc atcgcaaaca tcaacatcaa gaaagattcc | 60 |
| agttttgcta tgttgctgga agcacagcgt cgtggttacg aacttcacta tatggagatg | 120 |
| ggcgatctgt atctgatcaa tggtgaagcc cgcgcccata cccgcacgct gaacgtgaag | 180 |
| cagaactacg aagagtggtt ttcgttcgtc ggtgaacagg atctgccgct ggccgatctc | 240 |
| gatgtgatcc tgatgcgtaa agacccgccg tttgataccg agtttatcta cgcgacctat | 300 |
| attctggaac gtgccgaaga gaaagggacg ctgatcgtta caagccgca gagcctgcgc | 360 |
| gactgtaacg agaaactgtt taccgcctgg ttctctgact aacgccaga aacgctggtt | 420 |
| acgcgcaata aagcgcagct aaaagcgttc tgggagaaac acagcgacat cattcttaag | 480 |
| ccgctggacg gtatgggcgg cgcgtcgatt ttccgcgtga agaaggcga tccaaacctc | 540 |
| ggcgtgattg ccgaaacct gactgagcat ggcactcgct actgcatggc gcaaaattac | 600 |
| ctgccagcca ttaaagatgg cgacaaacgc gtgctggtgg tggatggcga ccgtaccg | 660 |
| tactgcctgg cgcgtattcc gcagggggc gaaacccgtg gcaatctggc tgccggtggt | 720 |
| cgcggtgaac tcgtccgct gacggaaagt gactggaaa tcgcccgtca gatcgggccg | 780 |
| acgctgaaag aaaagggct gatttttgtt ggtctggata tcatcggcga ccgtctgact | 840 |
| gaaattaacg tcaccagccc aacctgtatt cgtgagattg aagcagagtt tccggtgtcg | 900 |
| atcaccggaa tgttaatgga tgccatcgaa gcacgtttac agcagcagta a | 951 |

<210> SEQ ID NO 11
<211> LENGTH: 1245
<212> TYPE: DNA
<213> ORGANISM: Schizosaccharomyces pombe

<400> SEQUENCE: 11

| | |
|---|---|
| atgaacattg ttaaacgagc agtcccagaa ttactgagag gaatgaccaa tgcaacacca | 60 |
| aatatcggtt tgattaaaaa caaggtagta agctttgaag ctgtcggaca actcaaaaaa | 120 |
| tcttttaca aaagacaatt gcctaaacaa tgtttagctt ttgattcatc tctcggtaaa | 180 |
| gatgtttttt tacgagcatt gcaagaggga cggatgaaa attattttc gcttgcacag | 240 |
| cagatggtaa cccaaaacga accagctttt tgtggattgg gaactctctg catgattctt | 300 |
| aattcgctta agttgacccc gggtagatta tggaagggat cttggcgctg gtatgatcag | 360 |
| tatatgcttg attgttgtcg atcgctaagc gatattgaaa aagatggtgt tacgctagaa | 420 |
| gagttctctt gtttagctaa ctgcaatggc cttcggacta ttacgaaatg tgtcaaagat | 480 |
| gttagctttg atgaatttcg aaagacgta atctcttgtt ctaccattga aataaaatt | 540 |
| atggcaattt cattttgccg gaaagtgctc ggtcaaacag gcgatggaca ttttagtcca | 600 |
| gttggaggct tcagtgaaag tgataacaag atattaatat tggacgttgc tcgatttaaa | 660 |
| tatccttgct actgggtgga tttgaagctc atgtacgaga gtatgttttcc tatcgataaa | 720 |
| gctagcggcc aacctagagg ctatgtactt ttagagccaa tgcatattcc tttaggtgtg | 780 |

```
cttacagtcg gtttaaacaa gtacagctgg cgaaacgttt ccaagcatat actgcagcag    840
gcggcaacgg taaaaaacgc agacaatttg gctgaaatac ttttatccat taatcaatca    900
tcaattcctc taatccaaga acgctccaac agttcaaagt ctggtgattt cgagcatttt    960
aaagaatgta ttagaagcac aaaaacatat catttatttc tgaaacatac gaataccaat   1020
gttgaatata tcactatggc ttttttgggct atattttcct tacccatgat ccaaaaagcg   1080
cttcccaaag gcgttctaga agagattcaa tctttattga aagaagttga aatttccgaa   1140
attaacactc aactaactgc gttgaaaaaa cagcttgata gtttaaccca ttgttgtaaa   1200
actgacactg ggtgttgtag ttcaagctgc tgtaaaaata cgtga                   1245
```

<210> SEQ ID NO 12
<211> LENGTH: 1395
<212> TYPE: DNA
<213> ORGANISM: Arabidopsis thaliana

<400> SEQUENCE: 12

```
aagcttgcat gctgatctca aatacattga tacatatctc atctagatct aggttatcat     60
tatgtaagaa agttttgacg aatatggcac gacaaaatgg ctagactcga tgtaattggt    120
atctcaactc aacattatac ttataccaaa cattagttag acaaaattta aacaactatt    180
ttttatgtat gcaagagtca gcatatgtat aattgattca gaatcgtttt gacgagttcg    240
gatgtagtag tagccattat ttaatgtaca tactaatcgt gaatagtgaa tatgatgaaa    300
cattgtatct tattgtataa atatccataa acacatcatg aaagacactt tctttcacgg    360
tctgaattaa ttatgataca attctaatag aaaacgaatt aaattacgtt gaattgtatg    420
aaatctaatt gaacaagcca accacgacga cgactaacgt tgcctggatt gactcggttt    480
aagttaacca ctaaaaaaac ggagctgtca tgtaacacgc ggatcgagca ggtcacagtc    540
atgaagccat caaagcaaaa gaactaatcc aagggctgag atgattaatt agtttaaaaa    600
ttagttaaca cgagggaaaa ggctgtctga cagccaggtc acgttatctt tacctgtggt    660
cgaaatgatt cgtgtctgtc gattttaatt attttttga aaggccgaaa ataaagttgt    720
aagagataaa cccgcctata taaattcata tattttcctc tccgctttga attgtctcgt    780
tgtcctcctc actttcatca gccgttttga atctccggcg acttgacaga aagaacaag    840 gaagaagact aagagagaaa gtaagagata tccaggaga ttcattctcc gttttgaatc    900
ttcctcaatc tcatcttctt ccgctctttc tttccaaggt aataggaact ttctggatct    960
actttatttg ctggatctcg atcttgtttt ctcaatttcc ttgagatctg gaattcgttt   1020
aatttggatc tgtgaacctc cactaaatct tttggtttta ctagaatcga tctaagttga   1080
ccgatcagtt agctcgatta tagctaccag aatttggctt gaccttgatg gagagatcca   1140
tgttcatgtt acctgggaaa tgatttgtat atgtgaattg aaatctgaac tgttgaagtt   1200
agattgaatc tgaacactgt caatgttaga ttgaatctga acactgttta aggttagatg   1260
aagtttgtgt atagattctt cgaaacttta ggatttgtag tgtcgtacgt tgaacagaaa   1320
gctatttctg attcaatcag ggtttatttg actgtattga actcttttttg tgtgtttgca   1380 gctcataaac catgg                                                    1395
```

<210> SEQ ID NO 13
<211> LENGTH: 1266
<212> TYPE: DNA
<213> ORGANISM: Oryza sativa

<400> SEQUENCE: 13

```
tagctagcat actcgaggtc attcatatgc ttgagaagag agtcgggata gtccaaaata      60
aaacaaaggt aagattacct ggtcaaaagt gaaaacatca gttaaaaggt ggtataagta     120
aaatatcggt aataaaaggt ggcccaaagt gaaatttact cttttctact attataaaaa     180
ttgaggatgt tttgtcggta ctttgatacg tcattttttgt atgaattggt ttttaagttt    240
attcgcgatt tggaaatgca tatctgtatt tgagtcggtt tttaagttcg ttgcttttgt     300
aaatacagag ggatttgtat aagaaatatc tttaaaaaac ccatatgcta atttgacata     360
attttttgaga aaaatatata ttcaggcgaa ttccacaatg aacaataata agattaaaat    420
agcttgcccc cgttgcagcg atgggtattt tttctagtaa aataaaagat aaacttagac     480
tcaaaacatt tacaaaaaca acccctaaag tcctaaagcc caaagtgcta tgcacgatcc     540
atagcaagcc cagcccaacc caacccaacc caacccaccc cagtgcagcc aactggcaaa     600
tagtctccac ccccggcact atcaccgtga gttgtccgca ccaccgcacg tctcgcagcc     660
aaaaaaaaaa aaagaaagaa aaaaagaaa aagaaaaaca gcaggtgggt ccgggtcgtg      720
ggggccggaa aagcgaggag gatcgcgagc agcgacgagg cccggccctc cctccgcttc    780
caaagaaacg ccccccatcg ccactatata catccccccc cctctcctcc catccccccca   840
accctaccac caccaccacc accacctcct ccccccctcgc tgccggacga cgagctcctc   900
cccccctcccc ctccgccgcc gccggtaacc accccgcccc tctcctctctt ctttctccgt  960
ttttttttttc gtctcggtct cgatctttgg ccttggtagt ttgggtgggc gagagcggct   1020
tcgtcgccca gatcggtgcg cgggagggg gggatctcgc ggctggcgtc tccgggcgtg    1080
agtcggcccg gatcctcgcg gggaatgggg ctctcggatg tagatcttct ttctttcttc    1140
tttttgtggt agaatttgaa tccctcagca ttgttcatcg gtagttttc ttttcatgat    1200
ttgtgacaaa tgcagcctcg tgcggagctt ttttgtaggt agaagatggc tgacgccgag    1260
gatatc                                                              1266
```

<210> SEQ ID NO 14
<211> LENGTH: 1871
<212> TYPE: DNA
<213> ORGANISM: Glycine max

<400> SEQUENCE: 14

```
gagctccacc gcggtggcgg ccgctctaga gcgcgtcgac tcacattctt gcccgcctga      60
tgaatgctca tccggaattc agtggaagtg gtgcagaaga ggggagggaa tgtttggggt     120
acatgatttg aaaaaagggg agaatgatta gaagagatag aaaattggca gaccaacatt     180
gaaggattca taggaatgtt gtgtgctagt aaattggaca aatgttgctc ttgatatttt     240
cagcatatca ttcatcttag aagcccaact gttcttttttt atatatattc tctgttgcct    300
tccttttcctt caaaacacgg cttttgaatt ttgaaccatt aactgagttg gaatagtggt    360
aaaatcatgt agatttttct tttcgtttttg tggggatatg aatacgaaat atccttacaa    420
ccagacaaag ctgtggctca gaagaaagag aaacatgcct cactgctaga atcactagaa    480
ctcacatctt gtatacaaac tgttatacca aactgagaat tttacaattt ccaaagatgc    540
aattctcaac cattaaccaa tttcatctta aacactaaca gttcctcagt cttgaacttt    600
ccatgctgaa aatttgttgc ctatttcttt tataggcagt ggcttcttat gagagtcaca    660
ctctctgaac ttcttacgta atacttgact tttcatttttg tgctttataa ttgttatctc    720
atgcattgca cttttaagat aaggttgttg tgcattgttt ggttgagtgc aacgatttac    780
```

-continued

```
tgattaccat agctacttgt ggatcttata ttttcaaaag tgtatgcttg gtcattaatc        840
aaccaagcat gataagcccc atcatctacc accccttcta taccatatac gcattttgct        900
tatctacatt gctactgtta cactcaaaca agtctaacag ataatacgtt aagttaatga        960
acatttttag taatattatt ataaggattg gccaatgtaa ttgtgaagag agaagcatgc       1020
tttaagctac ccaacaaaat ggataagagt ttcagttgat atggttctct tgtttctttt       1080
ccaataaaaa accaacttta aaatataaaa tttactgtaa caaaggaaca aagagttttc       1140
acttaatcca tgaatgagaa aggatggtca caaaatatgt taggttaata tggaatgagg       1200
gcactgtgca aactacacaa ataatatcaa ttccaccacc atcacacatt tacgttcttc       1260
caaggaagag ataagataat ggagcctcca cgtgtcacct ccacatggta cctaacaata       1320
aggctaccat tcaaaatttt cctcactcgt gtggcctata tgctgtaatg tcatcactta       1380
ttcaatccaa cggttgtaac ttttcggcaa ccaatcctct ccatttcaca ccattggatt       1440
agtactacac aaatcacact attatatata gcaagtttga gcagaagcta ggatatctgg       1500
cagcagaaaa acaagtagtt ggatcctaag aagaagaaac catggcccgg aagcttgtc        1560 atttgaaaat ttgcaaagca tctgtagcca ccccactttg tttgttgtac ttaaactaca       1620
ttcccatttg tttttgcttt atgagatttc atcatcctgt attttggtt tctgttttcg        1680 gacttcaatg gaaattaatg gatgagaact aatgaataag ctattgtgtt gtgttgcttt       1740
gtttccaaat aacttcaaga acccattgtc cttgcatttc catcttgtgg gttgaaatta       1800
gtctcttcta aatttaagtt aattgtgtca ctaaatgatg gttaacaaag ctcgaggggg       1860
gcccggtacc c                                                            1871
```

```
<210> SEQ ID NO 15
<211> LENGTH: 47
<212> TYPE: DNA
<213> ORGANISM: Artificial Sequence
<220> FEATURE:
<223> OTHER INFORMATION: AtACR2 primer 1

<400> SEQUENCE: 15
tacgtcggat cctaaggagg atagaccatg gcgatggcga gaagcat                      47

<210> SEQ ID NO 16
<211> LENGTH: 48
<212> TYPE: DNA
<213> ORGANISM: Artificial Sequence
<220> FEATURE:
<223> OTHER INFORMATION: AtACR2 primer 2

<400> SEQUENCE: 16
taggtcctcg agttaggcgc aatcgccctt gcaaggaacc tctgcaca                     48

<210> SEQ ID NO 17
<211> LENGTH: 71
<212> TYPE: DNA
<213> ORGANISM: Artificial Sequence
<220> FEATURE:
<223> OTHER INFORMATION: OsACR2-1 primer 1

<400> SEQUENCE: 17
tacgtcggat ccaggaggta gaccatggcg cggagcgtgt cgtacgtgtc ggcggcgaag        60
ctcctggcaa t                                                            71

<210> SEQ ID NO 18
```

-continued

```
<211> LENGTH: 40
<212> TYPE: DNA
<213> ORGANISM: Artificial Sequence
<220> FEATURE:
<223> OTHER INFORMATION: OsACR2-1 primer 2

<400> SEQUENCE: 18
tagctgctcg agaagctttt acaactcagg ttcttcaggt                    40

<210> SEQ ID NO 19
<211> LENGTH: 49
<212> TYPE: DNA
<213> ORGANISM: Artificial Sequence
<220> FEATURE:
<223> OTHER INFORMATION: OsACR2-2 primer 1

<400> SEQUENCE: 19
tacgtcgaat tcaggaggta gaccatggcg aggggcgtct cctacgttt          49

<210> SEQ ID NO 20
<211> LENGTH: 40
<212> TYPE: DNA
<213> ORGANISM: Artificial Sequence
<220> FEATURE:
<223> OTHER INFORMATION: OsACR2-2 primer 2

<400> SEQUENCE: 20
tagctgctcg agaagctttc aagagcacac acccttgcaa                    40

<210> SEQ ID NO 21
<211> LENGTH: 396
<212> TYPE: DNA
<213> ORGANISM: Crambe abyssinica

<400> SEQUENCE: 21
atggcggcga gaagcatctc ttacatcacc tctactcagc tccttcctct tcatcgtcgt    60
cccaatatag ccatcatcga tgtcagggat gaagagagga actatgacgg gcatatagct   120
ggttcgctac gctatgcgag tggctctttt gatgacagga tctctcatct tgttcaacat   180
gttaaggata aagacacact tgtcttccat tgtgctttga gccaggttcg tggcccaacc   240
tgtgcaagaa gactcgtgaa ttatcttgac gagaagaaac aagaaactgg aataaaaaac   300
atcatgatcc tggaacgtgg cttcaatggc tgggaagctg ctggtaaacc ggtttgccgc   360
tgtgctgacg ttccttgcaa gggcgactgc acctaa                             396

<210> SEQ ID NO 22
<211> LENGTH: 131
<212> TYPE: PRT
<213> ORGANISM: Crambe abyssinica

<400> SEQUENCE: 22

Met Ala Ala Arg Ser Ile Ser Tyr Ile Thr Ser Thr Gln Leu Leu Pro
1               5                   10                  15

Leu His Arg Arg Pro Asn Ile Ala Ile Ile Asp Val Arg Asp Glu Glu
            20                  25                  30

Arg Asn Tyr Asp Gly His Ile Ala Gly Ser Leu Arg Tyr Ala Ser Gly
        35                  40                  45

Ser Phe Glu Asp Arg Ile Ser His Leu Val Gln Asn Val Lys Asp Lys
    50                  55                  60

Asp Thr Leu Val Phe His Cys Ala Leu Ser Gln Val Arg Gly Pro Thr
65                  70                  75                  80
```

-continued

```
Cys Ala Arg Arg Leu Val Asn Tyr Leu Asp Glu Lys Lys Gln Glu Thr
            85                  90                  95

Gly Ile Lys Asn Ile Met Ile Leu Glu Arg Gly Phe Asn Gly Trp Glu
        100                 105                 110

Ala Ala Gly Lys Pro Val Cys Arg Cys Ala Asp Val Pro Cys Lys Gly
        115                 120                 125

Asp Cys Thr
    130

<210> SEQ ID NO 23
<211> LENGTH: 45
<212> TYPE: DNA
<213> ORGANISM: Artificial Sequence
<220> FEATURE:
<223> OTHER INFORMATION: BnACR2 primer 1

<400> SEQUENCE: 23
tacgtcggat ccaggaggta gaccatggcg gcgagaagca tctct          45

<210> SEQ ID NO 24
<211> LENGTH: 40
<212> TYPE: DNA
<213> ORGANISM: Artificial Sequence
<220> FEATURE:
<223> OTHER INFORMATION: BnACR2 primer 2

<400> SEQUENCE: 24
tagctgctcg agaagctttt aggtgcagtc gcccttgcaa                 40

<210> SEQ ID NO 25
<211> LENGTH: 45
<212> TYPE: DNA
<213> ORGANISM: Artificial Sequence
<220> FEATURE:
<223> OTHER INFORMATION: CaACR2 primer 1

<400> SEQUENCE: 25
tacgtcggat ccaggaggta gaccatggcg gcgagaagca tctct          45

<210> SEQ ID NO 26
<211> LENGTH: 40
<212> TYPE: DNA
<213> ORGANISM: Artificial Sequence
<220> FEATURE:
<223> OTHER INFORMATION: CaACR2 primer 2

<400> SEQUENCE: 26
tagctgctcg agaagctttt aggtgcagtc gcccttgcaa                 40

<210> SEQ ID NO 27
<211> LENGTH: 130
<212> TYPE: PRT
<213> ORGANISM: Saccharomyces cerevisiae

<400> SEQUENCE: 27

Met Val Ser Phe Ile Thr Ser Arg Gln Leu Lys Gly Leu Ile Glu Asn
1               5                   10                  15

Gln Arg Lys Asp Phe Gln Val Val Asp Leu Arg Arg Glu Asp Phe Ala
            20                  25                  30

Arg Asp His Ile Thr Asn Ala Trp His Val Pro Val Thr Ala Gln Ile
        35                  40                  45

Thr Glu Lys Gln Leu Asn Gln Leu Ile Lys Gly Leu Ser Asp Thr Phe
    50                  55                  60
```

```
Ser Ser Ser Gln Phe Val Lys Val Ile Phe His Cys Thr Gly Ser Lys
65                  70                  75                  80

Asn Arg Gly Pro Lys Val Ala Ala Lys Phe Glu Thr Tyr Leu Gln Glu
                85                  90                  95

Glu Asp Ile Thr Ser Lys Phe Glu Ser Cys Ile Leu Val Gly Gly Phe
            100                 105                 110

Tyr Ala Trp Glu Thr His Cys Arg Glu Ser Asn Leu Lys Leu Ile Val
        115                 120                 125

Ser Gly
    130

<210> SEQ ID NO 28
<211> LENGTH: 141
<212> TYPE: PRT
<213> ORGANISM: Escherichia coli

<400> SEQUENCE: 28

Met Ser Asn Ile Thr Ile Tyr His Asn Pro Ala Cys Gly Thr Ser Arg
1               5                   10                  15

Asn Thr Leu Glu Met Ile Arg Asn Ser Gly Thr Glu Pro Thr Ile Ile
            20                  25                  30

His Tyr Leu Glu Thr Pro Pro Thr Arg Asp Glu Leu Val Lys Leu Ile
        35                  40                  45

Ala Asp Met Gly Ile Ser Val Arg Ala Leu Leu Arg Lys Asn Val Glu
    50                  55                  60

Pro Tyr Glu Glu Leu Gly Leu Ala Glu Asp Lys Phe Thr Asp Asp Arg
65                  70                  75                  80

Leu Ile Asp Phe Met Leu Gln His Pro Ile Leu Ile Asn Arg Pro Ile
            85                  90                  95

Val Val Thr Pro Leu Gly Thr Arg Leu Cys Arg Pro Ser Glu Val Val
            100                 105                 110

Leu Glu Ile Leu Pro Asp Ala Gln Lys Gly Ala Phe Ser Lys Glu Asp
        115                 120                 125

Gly Glu Lys Val Val Asp Glu Ala Gly Lys Arg Leu Lys
    130                 135                 140
```